US008999720B2

(12) United States Patent
Kristensen et al.

(10) Patent No.: US 8,999,720 B2
(45) Date of Patent: Apr. 7, 2015

(54) AQUEOUS RADIATION PROTECTING FORMULATIONS AND METHODS FOR MAKING AND USING THEM

(71) Applicant: Medtronic MiniMed, Inc., Northridge, CA (US)

(72) Inventors: Jesper Svenning Kristensen, Virum (DK); Soren Aasmul, Holte (DK)

(73) Assignee: Medtronic MiniMed, Inc., Northridge, CA (US)

( * ) Notice: Subject to any disclaimer, the term of this patent is extended or adjusted under 35 U.S.C. 154(b) by 187 days.

(21) Appl. No.: 13/660,648

(22) Filed: Oct. 25, 2012

(65) Prior Publication Data

US 2013/0130395 A1    May 23, 2013

Related U.S. Application Data

(60) Provisional application No. 61/561,146, filed on Nov. 17, 2011.

(51) Int. Cl.
| | |
|---|---|
| A61B 5/00 | (2006.01) |
| G01N 33/543 | (2006.01) |
| G01N 33/53 | (2006.01) |
| A61B 5/145 | (2006.01) |
| A61B 5/1455 | (2006.01) |
| A61B 5/1473 | (2006.01) |
| A61B 5/1486 | (2006.01) |
| A61L 2/02 | (2006.01) |

(52) U.S. Cl.
CPC ............ *A61B 5/14532* (2013.01); *A61B 5/1455* (2013.01); *A61B 5/14735* (2013.01); *A61B 5/14865* (2013.01); *A61L 2/02* (2013.01); *A61B 2562/12* (2013.01); *A61B 2562/18* (2013.01); *A61L 2202/14* (2013.01); *A61L 2202/24* (2013.01)

(58) Field of Classification Search
CPC ........ A61B 5/14532; A61B 5/14; A61B 5/00; A61B 5/14735; G01N 33/54366; G01N 33/543; G01N 33/53
USPC .......................... 436/95, 94, 93, 91; 422/22, 1
See application file for complete search history.

(56) References Cited

U.S. PATENT DOCUMENTS

| | | | |
|---|---|---|---|
| 4,755,173 A | 7/1988 | Konopka et al. | |
| 5,391,250 A | 2/1995 | Cheney, II et al. | |
| 5,485,408 A | 1/1996 | Blomquist | |
| 5,522,803 A | 6/1996 | Teissen-Simony | |
| 5,665,065 A | 9/1997 | Colman et al. | |
| 5,777,060 A | 7/1998 | Van Antwerp | |
| 5,800,420 A | 9/1998 | Gross et al. | |
| 5,807,375 A | 9/1998 | Gross et al. | |
| 5,925,021 A | 7/1999 | Castellano et al. | |
| 5,954,643 A | 9/1999 | Van Antwerp et al. | |
| 6,002,954 A | 12/1999 | Van Antwerp et al. | |
| 6,017,328 A | 1/2000 | Fischell et al. | |
| 6,186,982 B1 | 2/2001 | Gross et al. | |
| 6,232,130 B1 | 5/2001 | Wolf | |
| 6,246,992 B1 | 6/2001 | Brown | |
| 6,248,067 B1 | 6/2001 | Causey, III et al. | |
| 6,248,093 B1 | 6/2001 | Moberg | |
| 6,355,021 B1 | 3/2002 | Nielsen et al. | |
| 6,379,301 B1 | 4/2002 | Worthington et al. | |
| 6,544,212 B2 | 4/2003 | Galley et al. | |
| 6,558,351 B1 | 5/2003 | Steil et al. | |
| 6,591,876 B2 | 7/2003 | Safabash | |
| 6,641,533 B2 | 11/2003 | Causey, III et al. | |
| 6,736,797 B1 | 5/2004 | Larsen et al. | |
| 6,749,587 B2 | 6/2004 | Flaherty | |
| 6,766,183 B2 | 7/2004 | Walsh et al. | |
| 6,801,420 B2 | 10/2004 | Talbot et al. | |
| 6,804,544 B2 | 10/2004 | Van Antwerp et al. | |
| 7,003,336 B2 | 2/2006 | Holker et al. | |
| 7,029,444 B2 | 4/2006 | Shin et al. | |
| 7,066,909 B1 | 6/2006 | Peter et al. | |
| 7,137,964 B2 | 11/2006 | Flaherty | |
| 7,303,549 B2 | 12/2007 | Flaherty et al. | |
| 7,399,277 B2 | 7/2008 | Saidara et al. | |

(Continued)

FOREIGN PATENT DOCUMENTS

| | | |
|---|---|---|
| WO | 9109312 | 6/1991 |
| WO | 9719188 A1 | 5/1997 |

(Continued)

OTHER PUBLICATIONS

PCT International Search Report and Written Opinion dated Mar. 1, 2013 for PCT Application No. PCT/US2012/065073.
Kon, K., et al., "Lysosomal Iron Mobilization and Induction of the Mitochondrial Permeability Transition in Acetaminophen-Induced Toxicity to Mouse Hepatocytes", Toxicological Sciences, Sep. 1, 2010, pp. 101-108, vol. 117, No. 1., Oxford University Press.
Boukari et al., "Influence of persulfate ions on the removal of phenol in aqueous solution using electron beam irradiation". Journal of Hazardous Materials, vol. 185, (2011), pp. 844-851.
Davies, "Protein Damage and Degradation by Oxygen Radicals, I. General Aspects". The Journal of Biological Chemistry, vol. 262, No. 20, (Jul. 15, 1987), pp. 9895-9901.

(Continued)

*Primary Examiner* — Christine T Mui
(74) *Attorney, Agent, or Firm* — Gates & Cooper, LLP

(57) ABSTRACT

Medical devices are typically sterilized in processes used to manufacture such products and their sterilization by exposure to radiation is a common practice. Radiation has a number of advantages over other sterilization processes including a high penetrating ability, relatively low chemical reactivity, and instantaneous effects without the need to control temperature, pressure, vacuum, or humidity. Unfortunately, radiation sterilization can compromise the function of certain components of medical devices. For example, radiation sterilization can lead to loss of protein activity and/or lead to bleaching of various dye compounds. Embodiments of the invention provide methods and materials that can be used to protect medical devices from unwanted effects of radiation sterilization.

19 Claims, 19 Drawing Sheets

(56) References Cited

U.S. PATENT DOCUMENTS

| | | |
|---|---|---|
| 7,442,186 B2 | 10/2008 | Blomquist |
| 7,602,310 B2 | 10/2009 | Mann et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 2007/0123819 A1 | 5/2007 | Memoe et al. |
| 2007/0227907 A1 | 10/2007 | Shah et al. |
| 2008/0188723 A1 | 8/2008 | Kristensen et al. |
| 2009/0131773 A1 | 5/2009 | Struve et al. |
| 2009/0187084 A1 | 7/2009 | Kristensen et al. |
| 2009/0221891 A1 | 9/2009 | Yu et al. |
| 2010/0025238 A1 | 2/2010 | Gottlieb et al. |
| 2010/0160861 A1 | 6/2010 | Causey, III et al. |
| 2011/0034908 A1 | 2/2011 | Hyde et al. |
| 2011/0152654 A1 | 6/2011 | Wang et al. |
| 2011/0319734 A1 | 12/2011 | Gottlieb et al. |
| 2013/0060105 A1* | 3/2013 | Shah et al. .......... 600/316 |

FOREIGN PATENT DOCUMENTS

| | | |
|---|---|---|
| WO | 0002048 A1 | 1/2000 |
| WO | 0230275 A1 | 4/2002 |
| WO | 03006992 A1 | 1/2003 |
| WO | 2005110207 | 11/2005 |
| WO | 2006061207 A1 | 6/2006 |

OTHER PUBLICATIONS

Davies, "Protein Damage and Degradation by Oxygen Radicals, II. Modification of Amino Acids". The Journal of Biological Chemistry, vol. 262, No. 20, (Jul. 15, 1987), pp. 9902-9907.

Davies, "Protein Damage and Degradation by Oxygen Radicals, III. Modification of Secondary and Tertiary Structure". The Journal of Biological Chemistry, vol. 262, No. 20, (Jul. 15, 1987), pp. 9908-9913.

Marras, "Selection of Fluorophore and Quencher Pairs for Flourescent Nucleic Acid Hybridization Probes". Methods in Molecular Biology, vol. 335, (2006), pp. 3-16.

Parth et al., "Studies on the effect of electron beam radiation on the molecular structure of ultra-high molecular weight polyethylene under the influence of a-tocopherol with respect to its application in medical implants". Journal of Materials Science: Materials in Medicine, vol. 13, (2002), pp. 917-921.

Prutz et al., "The role of sulfur peptide functions in free radical transfer: a pulse radiolysis study". Int. J. Radiat. Biol., vol. 55, No. 4, (1989), pp. 539-556.

Vahdat et al., "Decomposition and decoloration of a direct dye by electron beam radiation". Radiation Physics and Chemistry, vol. 79 (2010) 33-35.

Holton, James M. "A beginner's guide to radiation damage." Journal of synchrotron radiation 16.2 (2009): 133-142.

Jensen et al. "Quantifying protein adsorption and function at nanostructured materials: Enzymatic activity of glucose oxidase at glad structured electrodes." Langmuir 28.30 (2012): 11106-11114.

Judge et al. "Continuous glucose monitoring using a novel glucose/galactose binding protein: results of a 12-hour feasibility study with the Becton Dickinson glucose/galactose binding protein sensor." Diabetes technology & therapeutics 13.3 (2011): 309-317.

Paek et al. "Label-free, needle-type biosensor for continuous glucose monitoring based on competitive binding." Biosensors and Bioelectronics 40.1 (2013): 38-44.

Wallis et al. "Molecular determinants of oligomer formation and complement fixation in mannose-binding proteins." Journal of Biological Chemistry 274.6 (1999): 3580-3589.

Wong et al. "Factors influencing ultraviolet and electron beam irradiation-induced free radical damage of ascorbic acid." Food chemistry 74.1 (2001): 75-84.

* cited by examiner

AQUEOUS RADIATION PROTECTING FORMULATIONS AND METHODS FOR MAKING AND USING THEM

CROSS REFERENCE TO RELATED APPLICATIONS

This application claims the benefit of U.S. provisional patent application No. 61/561,146, filed Nov. 17, 2011, the entire contents of which are incorporated herein by reference.

BACKGROUND OF THE INVENTION

1. Field of the Invention

This invention relates to medical devices useful in in vivo environments, in particular, methods and materials used to sterilize such devices prior to their implantation in vivo.

2. Description of Related Art

Medical personnel and patients commonly utilize a wide variety of pre-sterilized medical products, such as glucose sensors that are used by diabetic patients. In this context, a number of different sterilization processes are used with various medical products in order to kill microorganisms that may be present. Most sterilization processes require the sterilizing agent to systemically permeate the article being sterilized. These methods can include heat sterilization, where the object to be sterilized is subjected to heat and pressure, such as in an autoclave. The heat and pressure penetrates though the object being sterilized and after a sufficient time will kill the harmful microorganisms. Gases such as hydrogen peroxide or ethylene oxide are also used to sterilize objects. Sterilization methods also include those that use ionizing radiation, such as gamma-rays, x-rays, or energetic electrons to kill microorganisms.

Radiation has a number of advantages over other sterilization processes including a high penetrating ability, relatively low chemical reactivity, and instantaneous effects without the need to control temperature, pressure, vacuum, or humidity. Consequently, the sterilization of medical devices by exposure to radiation is a common practice. Medical devices composed in whole or in part of polymers are typically sterilized by various kinds of radiation, including, but not limited to, electron beam (e-beam), gamma ray, ultraviolet, infra-red, ion beam, and x-ray sterilization.

Electron-beam and gamma ray sterilization processes provide forms of radiation commonly used to kill microbial organisms on medical devices. However, when used to kill microorganisms, such radiation can alter the structure of functional macromolecules present in medical products including polymers such as proteins. High-energy radiation tends to produce ionization and excitation in polymer molecules, as well as free radicals. These energy-rich species can react with macromolecules present in medical products and undergo dissociation, abstraction, chain scission and cross-linking.

The deterioration of the performance of polymeric materials and other macromolecules in medical devices due to radiation sterilization has been associated with free radical formation during radiation exposure. Electron-beam and gamma ray radiation can therefore be problematical when used to sterilize medical device includes components that are radiation sensitive. This complicates the sterilization process and limits the range of designs or materials available for medical devices. Consequently, methods and formulations that can protect medical device materials from damage that can occur as a result of exposure to high-energy radiation are desirable.

SUMMARY OF THE INVENTION

As noted above, the sterilization of medical devices by exposure to radiation is a common practice. Unfortunately, radiation sterilization can compromise the function of certain components of some medical devices. In this context, embodiments of the invention provide methods and materials that can be used to protect medical devices from unwanted effects of radiation sterilization. While typical embodiments of the invention pertain to glucose sensors, the systems, methods and materials disclosed herein can be adapted for use with a wide variety of medical devices.

The invention disclosed herein has a number of embodiments. Typical embodiments of the invention comprise methods for inhibiting damage to a saccharide sensor that can result from a radiation sterilization process (e.g. electron beam irradiation) by combining the saccharide sensor with an aqueous radioprotectant formulation during the sterilization process. In common embodiments of the invention, the saccharide sensor comprises a saccharide binding polypeptide having a carbohydrate recognition domain and the aqueous radioprotectant formulation comprises a saccharide selected for its ability to bind the saccharide binding polypeptide. In certain embodiments of the invention, the saccharide sensor comprises a fluorophore; and the aqueous radioprotectant formulation comprises a fluorophore quenching composition selected for its ability to quench the fluorophore. In illustrative embodiments of the invention, the sensor is a glucose sensor and the saccharide binding polypeptide comprises mannan binding lectin, concanavalin A, glucose-galactose binding protein, or glucose oxidase. In certain methods of the invention, the sterilization process is performed under conditions selected so that the saccharide binds the saccharide binding polypeptide and/or the fluorophore quenching composition quenches the fluorophore in a manner that inhibits damage to the saccharide sensor that can result from the radiation sterilization process.

As discussed below, a number of compounds are useful in the radioprotectant formulations disclosed herein. In certain embodiments of the invention, the aqueous radioprotectant formulation comprises a saccharide such as glucose, mannose, fructose, melizitose, N-acetyl-D-glucosamine, sucrose or trehalose. In some embodiments, the aqueous radioprotectant formulation comprises an antioxidant selected from the group consisting of ascorbate, urate, nitrite, vitamin E, α-tocopherol or nicotinate methylester. In certain embodiment of the invention, the aqueous radioprotectant formulation comprises a buffering agent, for example, one selected from the group consisting of citrate, tris(hydroxymethyl)aminomethane (TRIS) and tartrate. In various embodiments of the invention the radioprotectant formulations can comprise additional agents such as surfactants, amino acids, pharmaceutically acceptable salts and the like.

Related embodiments of the invention include compositions of matter comprising a medical device combined with an aqueous radioprotective formulation. One illustrative embodiment of the invention is a composition of matter comprising a saccharide sensor that includes a saccharide binding polypeptide; and/or a fluorophore. In typical composition embodiments, a saccharide sensor is combined with an aqueous radioprotectant formulation comprising a saccharide, wherein the saccharide binds to the saccharide binding polypeptide. Optionally in such compositions, the saccharide sensor is combined with a fluorophore quenching compound in the aqueous radioprotective formulation.

A number of compounds can be combined with the saccharide sensors disclosed herein to form the radioprotectant compositions of the invention. In typical embodiments of the invention, the composition comprises a saccharide selected from the group consisting of glucose, mannose, fructose, melizitose, N-acetyl-D-glucosamine, sucrose or trehalose. In certain embodiment of the invention, the composition comprises a fluorophore quenching compound, for example, acetaminophen. In some embodiments of the invention, the composition comprises an antioxidant compound is selected from the group consisting of ascorbate, urate, nitrite, vitamin E, α-tocopherol or nicotinate methylester. In some embodiments of the invention, the composition comprises a surfactant, for example a polysorbate such as Tween 80. In certain embodiments of the invention, the composition comprises a buffering agent such as citrate, tris(hydroxymethyl)aminomethane (TRIS) or tartrate.

Other objects, features and advantages of the present invention will become apparent to those skilled in the art from the following detailed description. It is to be understood, however, that the detailed description and specific examples, while indicating some embodiments of the present invention are given by way of illustration and not limitation. Many changes and modifications within the scope of the present invention may be made without departing from the spirit thereof, and the invention includes all such modifications.

DETAILED DESCRIPTION OF THE EMBODIMENTS

Figures 1A, 1B, 1C:
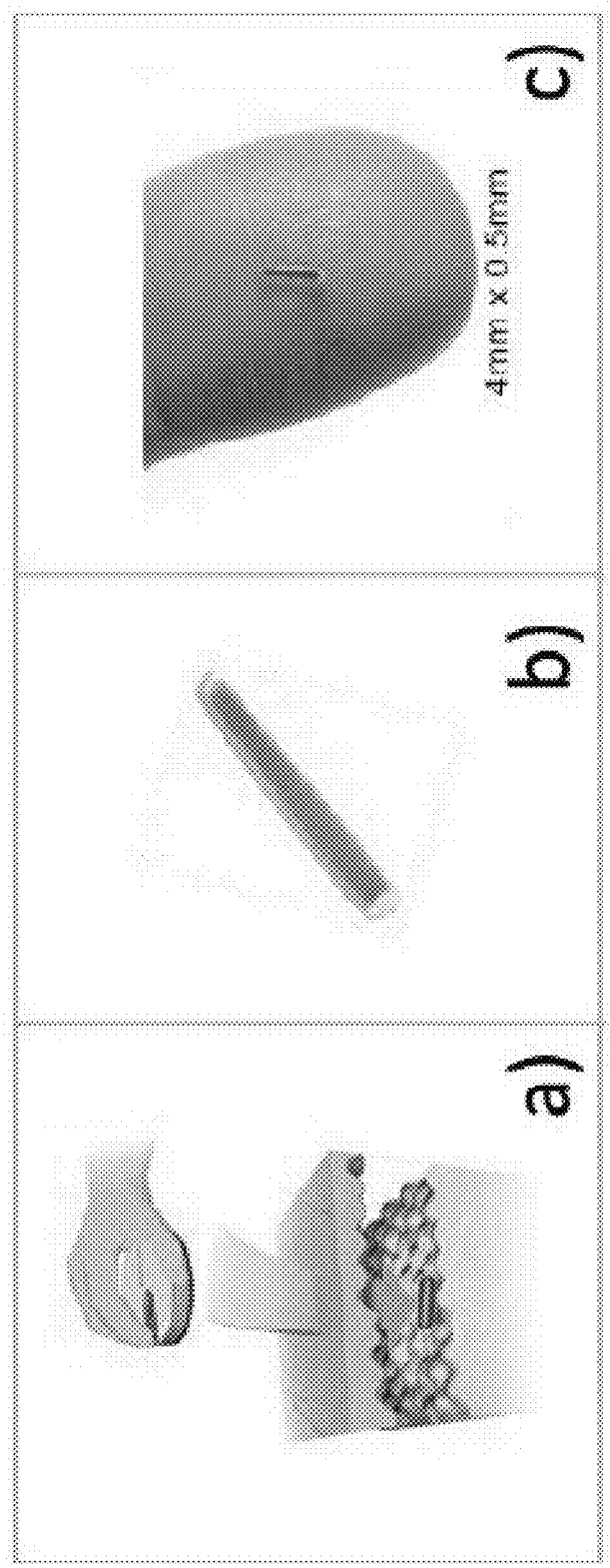
FIG. 1A shows a sensor design comprising a tubular capsule that is implanted under the skin and provides optical sensor in response to analyte (glucose).
FIG. 1B shows a view of this capsule.
FIG. 1C shows the relative size of this capsule.

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art. As appropriate, procedures involving the use of commercially available kits and reagents are generally carried out in accordance with manufacturer defined protocols and/or parameters unless otherwise noted. A number of terms are defined below.

The term "sensor" for example in "analyte sensor," is used in its ordinary sense, including, without limitation, means used to detect a compound such as an analyte. A "sensor system" includes, for example, elements, structures and architectures (e.g. specific 3-dimensional constellations of elements) designed to facilitate sensor use and function. Sensor systems can include, for example, compositions such as those having selected material properties, as well as electronic components such as elements and devices used in signal detection (e.g. optical detectors, current detectors, monitors, processors and the like). The term "sensing complex" as used herein refers to the elements of a sensor that interact with and generate a signal indicative of, a particular analyte (e.g. glucose and the like). The term "matrix" is used herein according to its art-accepted meaning of something within or from which something else is found, develops, and/or takes form. While typical embodiments of the invention pertain to glucose sensors used in the management of diabetes, the systems, methods and materials disclosed herein can be adapted for use with a wide variety of medical devices known in the art.

In the management of diabetes, the regular measurement of glucose in the blood is essential in order to ensure correct insulin dosing. Furthermore, it has been demonstrated that in the long term care of the diabetic patient better control of the blood glucose levels can delay, if not prevent, the onset of retinopathy, circulatory problems and other degenerative diseases often associated with diabetes. Thus, there is a need for reliable and accurate self-monitoring of blood glucose levels by diabetic patients. Typically, blood glucose is monitored by diabetic patients with the use of commercially available colorimetric test strips or electrochemical biosensors (e.g. enzyme electrodes), both of which require the regular use of a lancet-type instrument to withdraw a suitable amount of blood each time a measurement is made. On average, the majority of diabetic patients would use such instruments to take a measurement of blood glucose twice a day. However, the U.S. National Institute of Health has recommended that blood glucose testing should be carried out at least four times a day, a recommendation that has been endorsed by the American Diabetes Association. This increase in the frequency of blood glucose testing imposes a considerable burden on the diabetic patient, both in financial terms and in terms of pain and discomfort, particularly in the long-term diabetic who has to make regular use of a lancet to draw blood from the fingertips. Thus, there is clearly a need for a better long-term glucose monitoring system that does not involve drawing blood from the patient.

There have been a number of proposals for glucose measurement techniques that do not require blood to be withdrawn from the patient. One method for assaying glucose via competitive binding uses a proximity-based signal generating/modulating moiety pair which is typically an energy transfer donor acceptor pair (comprising an energy donor moiety and an energy acceptor moiety). The energy donor moiety is photoluminescent (usually fluorescent). In such methods, an energy transfer donor-acceptor pair is brought into contact with the sample (such as subcutaneous fluid) to be analyzed. The sample is then illuminated and the resultant emission detected. Either the energy donor moiety or the energy acceptor moiety of the donor-acceptor pair is bound to a receptor carrier (for example a carbohydrate binding molecule), while the other part of the donor acceptor pair (bound to a ligand carrier, for example a carbohydrate analogue) and any analyte (for example carbohydrate) present compete for binding sites on the receptor carrier. Energy transfer occurs between the donors and the acceptors when they are brought together. An example of donor-acceptor energy transfer is fluorescence resonance energy transfer (Förster resonance energy transfer, FRET), which is non-radiative transfer of the excited-state energy from the initially excited donor (D) to an acceptor (A). Energy transfer produces a detectable lifetime change (reduction) of the fluorescence of the energy donor moiety. Also, a proportion of the fluorescent signal emitted by the energy donor moiety is quenched. The lifetime change is reduced or even eliminated by the competitive binding of the analyte. Thus, by measuring the apparent luminescence lifetime, for example, by phase-modulation fluorometry or time resolved fluorometry (see Lakowicz, Principles of Fluorescence Spectroscopy, Plenum Press, 1983, Chapter 3), the amount of analyte in the sample can be determined. The intensity decay time and phase angles of the donor are expected to increase with increasing analyte concentration. An important characteristic of FRET is that it occurs over distances comparable to the dimensions of biological macromolecules. The distance at which FRET is 50% efficient, called the Förster distance, is typically in the range of 20-60 Å. Förster distances ranging from 20 to 90 Å are convenient for competitive binding studies. See, e.g. U.S. Pat. No. 6,232,120 and U.S. Patent Application Publication Nos. 20080188723, 20090221891, 20090187084 and 20090131773.

WO 91/09312 describes a subcutaneous method and device that employs an affinity assay based on glucose (incorporating an energy transfer donor acceptor pair) that is interrogated remotely by optical means. WO97/19188, WO 00/02048, WO 03/006992 and WO 02/30275 each describe glucose sensing by energy transfer, which produce an optical signal that can be read remotely. The systems discussed above rely on the plant lectin Concanavalin A (Con A) as the carbohydrate binding molecule. WO 06/061207 proposes that animal lectins such as mannose binding lectin (MBL) could be used instead. Previously disclosed carbohydrate analogues (e.g. those of U.S. Pat. No. 6,232,130) have comprised globular proteins to which carbohydrate and energy donor or energy acceptor moieties are conjugated. Carbohydrate polymers (e.g. optionally derivatized dextran and mannan) have also been used as carbohydrate analogues. In WO 06/061207 the use of periodate cleavage to allow binding of dextran to MBL at physiological calcium concentrations is disclosed. The assay components in such systems are typically retained by a retaining material. This may for example be a shell of biodegradable polymeric material, as described in WO 2005/110207.

Before implantable medical devices such as glucose sensors are introduced into the body, they must be sterilized. However, the materials of such devices, for example the assay components in sensors, can be sensitive to damage during sterilization. Heat sterilization causes denaturation of protein (lectin and/or carbohydrate analogue). Gas sterilization is difficult to use for wet devices such as the sensor. In view of this, the sterilization of medical devices by exposure to radiation is a common practice. Types of radiation which may be used in sterilization include gamma radiation and electron beam radiation. Electron beam radiation is easier to control than gamma radiation. However, electron beam radiation can lead to loss of protein activity and bleaching of dyes (e.g. a donor fluorophore and/or a acceptor dye). These effects can lead to loss of sensor activity.

Embodiments of the invention provide methods and materials that can be used to protect medical devices such as implantable glucose sensors from unwanted effects of radiation sterilization. The invention disclosed herein has a number of embodiments. Typical embodiments of the invention comprise methods for inhibiting damage to a medical device (e.g. a saccharide sensor) that can result from a radiation sterilization process by combining the medical device with an aqueous radioprotectant formulation during the sterilization process. In the context of embodiments of the invention as disclosed herein, because electron beam and gamma irradiation are fundamentally the same process, the protection provided by the methods and materials of the invention will be the same for these forms of irradiation. Gamma rays release secondary electrons from the materials around the item and hence create a cascade of electrons much like the e-beam. For this reason, gamma irradiation is suitable for sensors comprising one or more metal elements because metal is a good provider of secondary electrons. In some embodiments of the invention, the radiation sterilization process comprises electron beam irradiation. In some embodiments of the invention, the radiation sterilization process comprises gamma ray irradiation.

While the medical devices can be exposed to radiation supplied in multiple doses (e.g. 3×5 kGy for a total dose of 15 kGy), in typical embodiments of the instant invention, radiation is supplied in a single dose (e.g. 1×15 kGy for a total dose of 15 kGy). As disclosed herein (see, e.g. FIG. 2), supplying a sterilizing amount radiation in a single dose gives better radiation protection than supplying the same amount of radiation in multiple doses (dividing the radiation into a triple dose resulted in sensors having worse signal retention). Optionally, the total dose of radiation is not more than 35 kGy, and typically is in the range of. 10-20 kGy). In certain embodiments the total dose is 15 kGy±2 kGy. Gy (J/kg) is the SI unit of dose i.e. the amount of energy absorbed per unit mass. Following radiation exposure, sensor function parameters can be evaluated such as the sensor Dose Response (DR relative to 0 kGy DR) as well as the absolute DR (measured in degrees phase shift from 40 mg/dL glucose to 400 mg/dL glucose). In certain embodiments of the invention, an aqueous radiation protecting formulation functions to protect a glucose sensor from radiation damage so that the glucose sensor retains at least 50, 60 or 70% of its dose response (DR) to glucose following irradiation of the sensor (as compared to the DR of a control sensor that received no irradiation).

In some embodiments of the invention, the saccharide sensor comprises a boronic acid derivative such as those disclosed in U.S. Pat. Nos. 5,777,060, 6,002,954 and 6,766,183, the contents of which are incorporated herein by reference. In other embodiments of the invention, the saccharide sensor comprises a saccharide binding polypeptide. In certain embodiments of the invention the saccharide sensor comprises a lectin. Optionally the lectin is a C-type (calcium dependent) lectin. In some embodiments, the lectin is a vertebrate lectin, for example a mammalian lectin such as a human or humanized lectin. However, it may alternatively be a plant lectin, a bird lectin, a fish lectin or an invertebrate lectin such as an insect lectin. In certain embodiments, the lectin is in multimeric form. Multimeric lectins may be derived from the human or animal body. Alternatively, the lectin may be in monomeric form. Monomeric lectins may be formed by recombinant methods or by disrupting the binding between sub-units in a natural multimeric lectin derived from the human or animal body. Examples of this are described in U.S. Pat. No. 6,232,130. Saccharide sensors useful in embodiments of the invention are also disclosed in U.S. Patent Publication No. 2008/0188723, the contents of which are incorporated by reference.

In certain embodiments of the invention, the saccharide sensing element in a saccharide sensor comprises a lectin. Optionally, the lectin is mannose binding lectin, conglutinin or collectin-43 (e.g. bovine CL-43) (all serum collecting) or a pulmonary surfactant protein (lung collectins). Mannose binding lectin (also called mannan binding lectin or mannan binding protein, MBL, MBP), for example human MBL, has proved particularly interesting. MBL is a collagen-like defense molecule which comprises several (typically 3 to 4 (MALDI-MS), though distributions of 1 to 6 are likely to occur (SDS-PAGE)) sub-units in a "bouquet" arrangement, each composed of three identical polypeptides. Each sub-unit has a molecular weight of around 75 kDa, and can be optionally complexed with one or more MBL associated serine proteases (MASPs). Each polypeptide contains a CRD. Thus, each sub-unit presents three carbohydrate binding sites. Trimeric MBL and tetrameric MBL (which are the major forms present in human serum, Teillet et al., Journal of Immunology, 2005, page 2870-2877) present nine and twelve carbohydrate binding sites respectively. In typical embodiments of the invention, the lectin comprises polypeptides of *Homo sapiens* mannose-binding protein C precursor (NCBI Reference Sequence: NP_000233.1). Serum MBL is made of 3-4 subunits of 3 polypeptides each. The sequence of NCBI Reference Sequence: NP_000233.1 is between 27 kDa and 30 kDa giving the entire MBL protein a Mw typically of 270 kDa to 300 kDa.

Alternatively, the lectin may be a pulmonary surfactant protein selected from SP-A and SP-D. These proteins are similar to MBL. They are water-soluble collecting which act as calcium dependent carbohydrate binding proteins in innate host-defense functions. SP-D also binds lipids. SP-A has a "bouquet" structure similar to that of MBL (Kilpatrick D C (2000) Handbook of Animal Lectins, p. 37). SP-D has a tetrameric "X" structure with CRDs at each end of the "X". Other suitable animal lectins are known in the art such as PC-lectin CTL-1, Keratinocyte membrane lectins, CD94, P35 (synonym: human L-ficolin, a group of lectins), ERGIC-53 (synonym: MR60), HIP/PAP, CLECSF8, DCL (group of lectins), and the GLUT family proteins, especially GLUT1, GLUT4 and GLUT11. Further suitable animal lectins are set out in Appendices A, B and C of "Handbook of Animal Lectins: Properties and Biomedical Applications", David C. Kilpatrick, Wiley 2000.

In common embodiments of the invention, the saccharide sensor comprises a saccharide binding polypeptide having a carbohydrate recognition domain and the aqueous radioprotectant formulation comprises a saccharide selected for its ability to bind the saccharide binding polypeptide. In certain embodiments of the invention, the saccharide sensor comprises one or more fluorophores (e.g. a donor and/or a reference fluorophore); and the aqueous radioprotectant formulation comprises a fluorophore quenching compound selected for its ability to quench the fluorophore(s). Optionally, the sensor comprises at least one of protein/polypeptide, at least one energy donor, and/or at least one energy acceptor and this sensor is combined with at least one protective substance. In some embodiments the sensor comprises a protein, a fluorescent dye, dextran and a polymeric material. In illustrative embodiments of the invention, the sensor is a glucose sensor and the saccharide binding polypeptide comprises a mannan binding lectin, a concanavalin A, a glucose oxidase, or a glucose-galactose binding protein (see, e.g. U.S. Pat. No. 6,232,130; U.S. Patent Publication No. 2008/0188723; Jensen et al., Langmuir. 2012 Jul. 31; 28(30):11106-14. Epub 2012; Paek et al., Biosens Bioelectron. 2012 and Judge et al., Diabetes Technol Ther. 2011 March; 13(3):309-17, 2011, the contents of which are incorporated by reference).

As discussed below, a number of compounds are useful in the radioprotectant formulations disclosed herein. In certain embodiments of the invention, the aqueous radioprotectant formulation comprises a sugar such as glucose, mannose, fructose, melizitose, N-acetyl-D-glucosamine, sucrose or trehalose. In some embodiments, the aqueous radioprotectant formulation comprises an antioxidant selected from the group consisting of ascorbate, urate, nitrite, vitamin E, α-tocopherol or nicotinate methylester. In certain embodiment of the invention, the aqueous radioprotectant formulation comprises a buffering agent, for example, one selected from the group consisting of citrate, tris(hydroxymethyl)aminomethane (TRIS) and tartrate.

In typical methods of the invention, the sterilization process is performed under conditions selected to protect the functional integrity of the sterilized sensor. For example, in typical embodiments of the invention, the sterilization process is performed during or after cooling the device. In illustrative embodiments, the sterilization process is performed below a certain temperature or within a particular range of temperatures, for example below 10° C. or below 5° C. or at a temperature between 0 and 5° C., or between 0 and 10° C. In some embodiments of the invention, the sterilization process is performed under oxygen free conditions (e.g. when a formulation does not comprise an oxidizing compound). Optionally, the process is performed on a sensor within and aqueous formulation that has been de-aerated with argon gas, nitrogen gas, or the like. In some embodiments of the invention, the sterilization process is performed using a formulation having a pH below 7, below 6, or below 5 etc. In some embodiments of the invention, the sterilization process is performed under conditions selected so that the saccharide binds the saccharide binding polypeptide and/or the fluorophore quenching composition quenches the fluorophore so as to inhibit damage to the saccharide sensor that can result from the radiation sterilization process. Some methodological embodiments of the invention comprise further steps, for example those where an irradiated sensor composition comprising the aqueous radiation protecting formulation is dialyzed to alter the concentrations of one or more components in the formulation.

Another embodiment of the invention is a composition of matter comprising a saccharide sensor and a fluorophore. The saccharide sensing element of the saccharide sensor can comprise a boronic acid derivative, a molecular imprinted polymer or a polypeptide. In such compositions, the saccharide sensor is combined with a fluorophore quenching compound. One illustrative embodiment of the invention is a composition of matter comprising a saccharide sensor that includes a saccharide binding polypeptide having a carbohydrate recognition domain; and a fluorophore. In such compositions, the saccharide sensor is combined with an aqueous radioprotectant formulation comprising a saccharide, wherein the saccharide binds to the carbohydrate recognition domain. Optionally in such compositions, the saccharide sensor is also combined with a fluorophore quenching compound.

A number of compounds can be combined with the saccharide sensors disclosed herein to form the radioprotectant compositions of the invention. In typical embodiments of the invention, the composition comprises a saccharide selected from the group consisting of glucose, mannose, fructose, melizitose, N-acetyl-D-glucosamine, GluNac, sucrose or trehalose. In certain embodiment of the invention, the composition comprises a fluorophore quenching compound, for example, acetaminophen. In some embodiments of the invention, the composition comprises an antioxidant compound is selected from the group consisting of ascorbate, urate, nitrite, vitamin E, α-tocopherol or nicotinate methylester. In some embodiments of the invention, the composition comprises a surfactant, for example a polysorbate such as Tween 80. In certain embodiments of the invention, the composition comprises a buffering agent such as citrate, tris(hydroxymethyl) aminomethane (TRIS) or tartrate. Optionally the composition is formed to have a pH of 7 or below, 6 or below, or 5 or below.

Specific compounds are observed to provide saccharide sensors (e.g. those shown in FIGS. 1A-1C) with high levels of protection against radiation damage when present in aqueous radioprotectant formulations in a particular concentration range. For example, in certain embodiments of the invention, the radiation protecting formulation comprises acetaminophen in a concentration of at least 1 mM to 50 mM (e.g. at least 10 mM, at least 20 mM, at least 30 mM, at least 40 mM etc.). Optionally, the radiation protecting formulation comprises acetaminophen in a concentration of 20 mM±10 mM (and typically ±5 mM). In certain embodiments of the invention, the radiation protecting formulation comprises sucrose in a concentration of at least 10 mM to 1000 mM (e.g. at least 100 mM, at least 200 mM, at least 300 mM, at least 400 mM etc.). Optionally, the radiation protecting formulation comprises sucrose in a concentration of 500 mM±200 mM (and typically ±100 mM). In certain embodiments of the invention, the radiation protecting formulation comprises mannose in a concentration of at least 1 mM to 100 mM (e.g. at least 10 mM, at least 20 mM, at least 30 mM, at least 40 mM etc.). Optionally, the radiation protecting formulation comprises mannose in a concentration of 50 mM±20 mM (and typically ±10 mM). In certain embodiments of the invention, the radiation protecting formulation comprises ascorbate in a concentration of at least 1 mM to 100 mM (e.g. at least 10 mM, at least 20 mM, at least 30 mM, at least 40 mM etc.). In certain embodiments of the invention, the radiation protecting formulation comprises ascorbate in a concentration of not more than 10 mM, 20 mM, 30 mM, 40 mM, 50 mM, 60 mM, 70 mM, 80 mM, 90 mM or 100 mM. Optionally, the radiation protecting formulation comprises ascorbate in a concentration of 50 mM±20 mM (and typically ±10 mM). In certain embodiments of the invention, the radiation protecting formulation comprises Tris in a concentration of at least 1 mM to 10 mM (e.g. at least 1 mM, at least 2 mM, at least 3 mM, at least 4 mM etc.). Optionally, the radiation protecting formulation comprises Tris in a concentration of 5 mM±2 mM (and typically ±1 mM). In certain embodiments of the invention, the radiation protecting formulation comprises citrate in a concentration of at least 5 mM to 100 mM (e.g. at least 10 mM, at least 20 mM, at least 30 mM, at least 40 mM etc.). Optionally, the radiation protecting formulation comprises citrate in a concentration of 10 mM±2 mM (and typically ±1 mM).

As shown by the working embodiments disclosed herein, one or more of these compounds is typically combined with another of these compounds in the radiation protecting formulations of the invention. For example, certain formulations of the invention will comprise sucrose combined with acetaminophen and/or ascorbate and/or Tris and/or citrate. Similarly, certain formulations of the invention will comprise acetaminophen combined with sucrose and/or ascorbate and/or Tris and/or citrate. Similarly, certain formulations of the invention will comprise ascorbate combined with sucrose and/or acetaminophen and/or Tris and/or citrate. Similarly, certain formulations of the invention will comprise citrate combined with sucrose and/or acetaminophen and/or Tris and/or ascorbate. The formulations can comprise additional compositions such as one or more amino acids or pharmaceutically acceptable salts, for example those disclosed in Remington: The Science and Practice of Pharmacy, University of the Sciences in Philadelphia (Ed), 21$^{st}$ Edition (2005). As the sensor is to be used in the body, in typical embodiments, the excipients are commonly acceptable for use in the body.

As noted above, embodiments of the invention disclosed herein provide methods and materials useful in sterilization procedures for medical devices such as glucose sensors. While glucose sensors are the common embodiment discussed herein, embodiments of the invention described herein can be adapted and implemented with a wide variety of medical devices. As discussed in detail below, typical sensors that benefit from the methods and materials of the invention include, for example, those having sensing complexes that generate an optical signal that can be correlated with the concentration of an analyte such as glucose. A number of these sensors are disclosed, for example in U.S. Patent Application Publication Nos. 20080188723, 20090221891, 20090187084 and 20090131773, the contents of each of which are incorporated herein by reference. Embodiments of the invention described herein can also be adapted and implemented with amperometric sensor structures, for example those disclosed in U.S. Patent Application Publication Nos. 20070227907, 20100025238, 20110319734 and 20110152654, the contents of each of which are incorporated herein by reference.

The compositions used in embodiments of the invention exhibit a surprising degree of flexibility and versatility, characteristics which allow them to be adapted for use in a wide variety of sensor structures. In some embodiments of the invention, one or more sensor elements can comprise a structure formed from a polymeric composition through which water and other compounds such as analytes (e.g. glucose) can diffuse. Illustrative polymeric compositions are disclosed in U.S. Patent Publication No. 20090221891 and include, for example, material (e.g. one that is biodegradable) comprising a polymer having hydrophobic and hydrophilic units. Specific polymers can be selected depending upon a desired application. For example, for mobility of glucose, a material can be selected to have a molecular weight cut-off limit of no more than 25000 Da or no more than 10000 Da. Components disposed within such polymeric materials (e.g. sensing complexes) can be of high molecular weight, for example proteins or polymers, in order to prevent their loss from the sensor by diffusion through the polymeric materials. In an illustrative embodiment, hydrophilic units of a polymeric material comprise an ester of polyethylene glycol (PEG) and a diacid, and the molecular weight cut-off limit is affected by the PEG chain length, the molecular weight of the polymer and the weight fraction of the hydrophilic units. The longer the PEG chains, the higher the molecular weight cut-off limit, the higher the molecular weight of the polymer, the lower the molecular weight cut-off limit, and the lower the weight fraction of the hydrophilic units, the lower the molecular weight cut-off limit.

Sensor components can be selected to have properties that facilitate their storage and or sterilization. In some embodiments of the invention, all components of the sensor are selected for an ability to retain sensor function following a sterilization procedure (e.g. e-beam sterilization). In some embodiments of the invention, all components of the sensor are selected for an ability to retain sensor function following a drying procedure (e.g. lyophilization).

In illustrative embodiments of the invention, the sensor comprises a cylindrical/tubular architecture and has a diameter of less than 1 mm, 0.9 mm, 0.8 mm, 0.7 mm, 0.6 mm, 0.5 mm, 0.4 mm, 0.3 mm or 0.2 mm. Illustrative sensors of this type are shown in FIG. 1. In certain examples, the sensor has a diameter of about 0.5 mm or about 0.25 mm. In some embodiments, the body of sensor is formed from a polymeric material. Optionally, the sensor is in the form of a fiber. In some embodiments of the invention, the internal matrix of a cylindrical sensor comprises one or more cavities or voids, for example an encapsulated longitudinal cavity.

Optionally the sensing complex produces an optical signal that can be correlated with an analyte of interest, for example, glucose. A sensing complex (e.g. one comprising a binding assay) generating the optical signal should typically be reversible such that a continuous monitoring of fluctuating levels of analyte can be achieved. Optionally, the detectable or measurable optical signal is generated using a proximity based signal generating/modulating moiety pair so that a signal is generated or modulated when a first member of the pair is brought into close proximity with a second member of the pair. In one illustrative embodiment, the analyte binding agent (e.g. a lectin such as mannose binding lectin as disclosed in WO 2006/061207) is labelled with one of a proximity based signal generating/modulating moiety pair and the analyte analogue is labelled with the other of the proximity based signal generating/modulating moiety pair, and there is a detectable difference in signal when the analyte analogue and analyte binding agent form the complex and when the analyte analogue is displaced by the analyte from the complex. Typically, the proximity based signal generating/modulating moiety pair is an energy donor moiety and energy acceptor moiety pair. Energy donor moieties and energy acceptor moieties are also referred to as donor and acceptor chromophores (or light absorbing materials) respectively. An energy acceptor which does not emit fluorescence is referred to as a quenching moiety. In such embodiments, a lectin can be labelled with one of an energy donor and energy acceptor moiety pair and the analyte analogue is labelled with the other of the energy donor and energy acceptor moiety pair. The detectable difference in signal corresponds to a detectable difference in energy transfer from the energy donor moiety to the energy acceptor moiety. Optionally, the analyte analogue bears the energy acceptor moiety and the analyte binding agent bears the energy donor moiety. In certain embodiments of the invention, the sensor of the invention incorporates an assay which generates an optical readout using the technique of fluorescence resonance energy transfer (FRET).

In one illustrative embodiment of the sensors discussed in the paragraph above, the variants of the competitive binding assay each comprise: an analyte binding agent labelled with a first light-absorbing material; a macromolecule labelled with a second light-absorbing material and comprising at least one analyte analogue moiety; wherein the analyte binding agent binds at least one analyte analogue moiety of the macromolecule to form a complex from which said macromolecule is displaceable by said analyte, and wherein said complex is able to absorb light energy and said absorbed light energy is able to be non-radiatively transferred between one of the light-absorbing materials and the other of the light-absorbing materials with a consequent measurable change in a fluorescence property of said light absorbing materials when present in said complex as compared to their said fluorescence property when said macromolecule is displaced by said analyte from said complex, and wherein the different variants of the assay are distinguished by the number of analyte analogue moieties present in the macromolecule. Such sensors are disclosed, for example in U.S. Patent Application Publication Nos. 20080188723, 20090221891, 20090187084 and 20090131773, the contents of each of which are incorporated herein by reference.

In other embodiments of the invention, the sensor comprises planar layered elements and, for example comprises a conductive layer including an electrode, an analyte sensing layer disposed over the conductive layer (e.g. one comprising glucose oxidase); and an analyte modulating layer disposed over the analyte sensing layer. In certain embodiments of the invention, the sensor electrode is disposed within a housing (e.g. a lumen of a catheter). The sensor embodiment shown in FIG. 1D is a amperometric sensor 100 having a plurality of layered elements including a base layer 102, a conductive layer 104 which is disposed on and/or combined with the base layer 102. Typically the conductive layer 104 comprises one or more electrodes. An analyte sensing layer 110 (typically comprising an enzyme such as glucose oxidase) is disposed on one or more of the exposed electrodes of the conductive layer 104. A protein layer 116 disposed upon the analyte sensing layer 110. An analyte modulating layer 112 is disposed above the analyte sensing layer 110 to regulate analyte (e.g. glucose) access with the analyte sensing layer 110. An adhesion promoter layer 114 is disposed between layers such as the analyte modulating layer 112 and the analyte sensing layer 110 as shown in FIG. 1D in order to facilitate their contact and/or adhesion. This embodiment also comprises a cover layer 106 such as a polymer coating can be disposed on portions of the sensor 100. Apertures 108 can be formed in one or more layers of such sensors. Amperometric glucose sensors having this type of design are disclosed, for example are disclosed, for example, in U.S. Patent Application Publication Nos. 20070227907, 20100025238, 20110319734 and 20110152654, the contents of each of which are incorporated herein by reference.

Embodiments of the invention can be used with sensors having a variety of configurations and/or sensing complexes. In certain methodological embodiments of the invention, the sensor comprises a cylindrical polymeric material having a diameter of less than 1 mm, less than 0.5 mm or less than 0.25 mm, the internal matrix comprises an encapsulated longitudinal cavity, and the sensing complex comprises a carbohydrate binding lectin (e.g. mannose binding lectin which binds glucose) coupled to a fluorophore pair. In other methodological embodiments of the invention, the sensor comprises an electrode coated with glucose oxidase and a glucose limiting membrane disposed over the glucose oxidase, wherein the glucose limiting membrane modulates the diffusion of glucose therethrough.

Various publication citations are referenced throughout the specification. The disclosures of all citations in the specification are expressly incorporated herein by reference. All numbers recited in the specification and associated claims that refer to values that can be numerically characterized can be modified by the term "about".

EXAMPLES

Example 1

Illustrative Methods and Materials for Use with Embodiments of the Invention

Sterilization of medical devices is important and the choice of sterilization method is based on which methods would be both safe and least destructive to the medical device. Three methods of sterilization are commonly used with medical devices. These are heat sterilization, gas sterilization and radiation sterilization. Heat sterilization can be problematical for devices that include proteins because the heat can denature the proteins (protein unfolding happens at approx. 60° C.). Gas sterilization process can be difficult to use in medical devices that end up as a wet device because getting a gas into even small amounts of liquid (and out again) can be difficult. For these reasons radiation sterilization is a method of choice for use with many devices such as the glucose sensors discussed herein. Moreover, as e-beam is typically easier to control than gamma radiation, e-beam radiation is used in the illustrative examples disclosed herein. As noted below, e-beam radiation of protein containing solutions can lead to a loss of protein activity in these sensors. In addition, e-beam radiation of dyes can lead to bleaching of the dyes. Both these effects can contribute to losses in sensor activity.

In aqueous solutions, the radiolysis of water can initiate oxidation reactions of compounds dissolved in water. The treatment of aqueous solutions by electron beam irradiation can decrease the concentration of certain compounds, provided that the energy absorbed (dose) is sufficient.

During radiolysis (e.g. electron beam; eb) $H_2O$ turns into the following species:
OH., eaq, H., $H_3O+$, $H_2$, $H_2O_2$

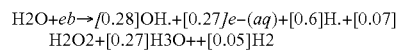

(brackets show the formation of species in μmoles/J) These entities formed by the radiolysis of water initiate many reactions with compounds present and in literature phenol degradation is often used as model compound to study the effect of the radiolysis.

The ionization of the assay components themselves in the solution is minimal compared to the radiolysis of the aqueous solvent since the concentration of assay is in the range of μM and the concentration of water will be approx. 55 M, i.e. the damaging effects of electron beam radiation to the assay origins from attack from water radiolysis products. In the optical sensor assay the protein appears in the concentration of μM i.e. water is present is $10^7$ times the concentration of protein.

As discussed in detail below, a number of compounds were identified and tested to assess their ability to protect sensors against radiation damage.

Protection of Polymers

Embodiments of the invention are designed to protect sensors that comprise polymers such as PolyActive™. PolyActive™ is a biodegradable polymeric drug delivery system. PolyActive represents a series of poly(ether ester) multiblock copolymers, based on poly(ethylene glycol), PEG, and poly(butylene terephthalate), PBT.

Polymers such as PolyActive™ can be protected against radiation damages by the presence of α-tocopherol. The α-tocopherol is added to the polymer by the manufacturer and is an antioxidant (Vitamin E) often used to protect products against radiation damage. In the PolyActive polymer used in the optical sensor it is expected that the α-tocopherol predominantly will be in the lipophilic domains of the polymer.

Decoloration of Dyes

Embodiments of the invention are designed to protect sensors that comprise dyes such as Alexa Fluor® fluorescent dyes. Decoloration of dye containing water, happens when the extensive electron conjugated system of the dye molecules is destroyed. The presence of radicals in the solution can initiate this process.

Protein Degradation

Embodiments of the invention are designed to protect sensors that comprise proteins such as MBL. Radiation damages to proteins are most often initiated by the damage of the disulphide bond RSSR formed by the cysteine residues. Cysteine amino acids are the most affected amino acid by radiation. Radiation damages occur when disulfide bridges break and carbonyl groups of acidic residues lose their definition thus causing the proteins to lose their activity.

The MBL protein has cysteine rich N-terminal domains (see, e.g. NCBI Reference Sequence: NP_000233.1). The tertiary structure of MBL is maintained by the RSSR bridges in the N-Terminal and if these are broken the structure of the protein and hence the function of the protein is lost. Wallis et al., J Biol Chem 274: 3580 (1999) shows a schematic of a polypeptide unit of MBL. In order to protect the protein from radiation damages one can endeavor to protect the cysteine residues of the N-Terminal and the CRD's.

Protection Against Radiation Damages

Art teaches that the prime species that damages proteins and other molecules in solution is the OH. (hydroxyl radical) hence this is the species to look for during protection. Antioxidants such as ascorbate can be used to protect proteins from damages by ionizing radiation. Prior art shows that the concentration of ascorbate used to protect the proteins is 0.2 M or higher, most likely due to the need for continuous antioxidant protection.

Antioxidants (e.g. ascorbate) have been described in literature for use in radiation protection of dyes. Vandat et al., Radiation Physics and Chemistry 79 (2010) 33-35 reports that electron beam irradiation induced oxidation leading to decoloration and decomposition of the dye C.I. Direct Black 22. Holton, J. Synchotron Rad. (2009), 16, 133-142 reports that ascorbate, nicotinic acid, DNTB, nitrate ion, 1,4-benzoquinone, TEMP and DTT have a protective effect against radiation damage to protein crystals. Wong et al., Food Chemistry 74 (2001) 75-84 reports the effect of L-ascorbic acid (LAA) on oxidative damage to lipid (linoleic acid emulsion) caused by electron beam radiation.

Ascorbate Action

The mechanism of action of protectants is to, for example, scavenge the radicals formed by radiolysis. The ascorbate is capable of reducing the hydroxyl radical. The ascorbate radical will undergo several processes e.g. disproportionately to ascorbate and dehydro-ascorbate (DHA). Due to this possible mode of action (ascorbate radical acting both as oxidizer and reducer) too high a concentration of ascorbate could be damaging to the chemistry of certain sensor embodiments.

Acetaminophen Action

Acetaminophen is easily oxidized in aqueous solution and hence is able to reduce radicals in solution. Since this compound also works as a fluorescence quencher for the AF594 donor fluorophore and AF700 reference fluorophore in a glucose assay system with these components, it appears that acetaminophen protects the dyes from bleaching due to its presence near the lipophilic areas of both the protein and the dyes.

Acetaminophen is more lipophilic than ascorbate and could hence act as a lipophilic radical scavenger primarily protecting the vulnerable domains (RSSR bridges and aromatic systems of the dyes) close to lipophilic domains in the compounds needing protection. This predominant lipophilic protection from acetaminophen combined with ascorbate's high solubility in aqueous solution protecting the more hydrophilic domains can be a powerful combination when looking for protection.

Sucrose and Mannose

Polyols like mannitol may be good radical scavenges and hence such carbohydrates also could yield some protection against radiation damages (hydrophilic domains). Further sucrose is known to have a stabilizing effect on the MBL hence this could help to improve the storage stability of the assay and mannose would bind to the CRD and create some stabilization effect here. Indeed carbohydrates add protective effects to the assay.

Buffer System:

Amine containing buffer systems like Tris and HEPES are known to provide some protection to the proteins. Especially they provide protection against tryptophan loss from proteins. We also observe protective effects from Tris buffer. Using Citrate as part of the buffer system keeps pH around 6 during storage. Citrate is a tertiary alcohol and alcohols like t-butanol (a tertiary alcohol) and isopropyl alcohol (a secondary alcohol) is known scavengers for radiolysis radicals.

In initial e-beam experiments, sterilization at a 15 kGy dose was used for the optical glucose sensor, one that comprises both MBL and fluorophore compositions. The conclusion was further that we would continue to identify and test excipients first for their individual protection capability and later take the best from each class and use them in combination.

Figure 2:
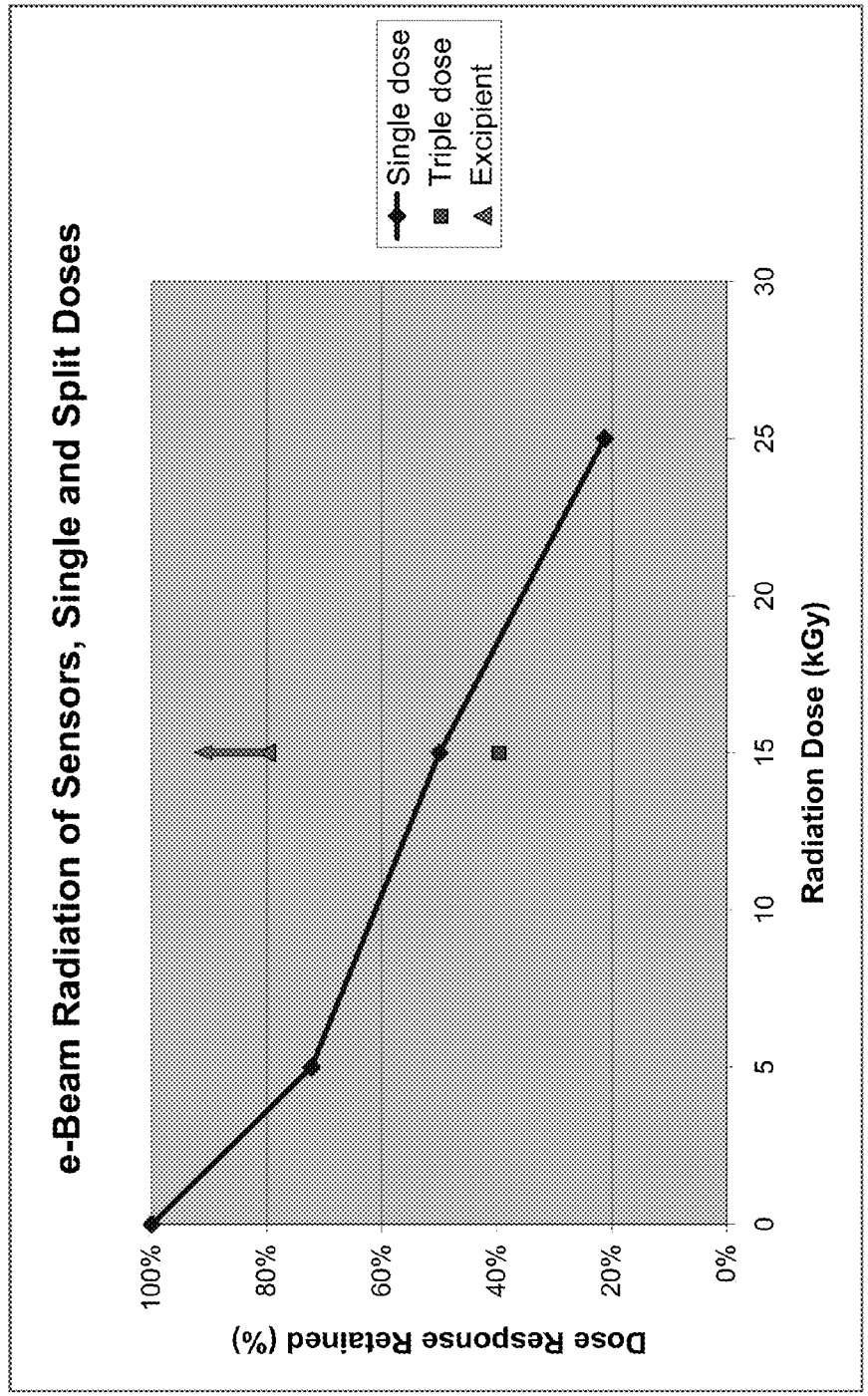
FIG. 2 shows a bar graph of data presenting dose response (DR) retention as a function of ebeam radiation dose for non-formulated sensors (control sensors not combined with any radioprotectant compositions), triple dose and formulated sensors at 15 kGy. The triple dose is 3×5 kGy. The sensors tested were radiated wet in a solution comprising 50 mM Tris-buffer saline. The arrow symbolizes that we can retain +80% of DR after exposure to 15 kGy for formulated sensors.

The following experiments were all conducted with radiation dose of 15 kGy while the sensors were cooled and oxygen free (except when the excipient was an oxidizing compound). After radiation the performance of the sensors was evaluated. The primary parameters evaluated as being retained was the Dose Response (DR relative to 0 kGy DR) as well as the absolute DR (measured in degrees phase shift from 40 mg/dL glucose to 400 mg/dL glucose) after the 15 kGy radiation dose. Also, sensor signal drift after radiation was observed but not quantified. The first initial experiments with sterilizing unformulated sensors (control sensors not combined with any radioprotectant compositions) yielded the results shown in FIG. 2. FIG. 2 shows a graph of data from experiments observing a retained dose response for unformulated sensors as a function of e-beam doses. The triple dose is 3×5 kGy. The sensors tested were radiated wet in a solution comprising 50 mM Tris-buffer saline.

A dose of 15 kGy as target for the radiation dose is a reasonable choice as there is still 50% retention of DR after irradiation of the unformulated fluorescent sensors. In addition the electrochemical sensors discussed herein are irradiated with 16 kGy if they have a low bioburden after production (<1.5 cfu). Due to the simplicity of the production of the optical sensor we expect this low bioburden to be the rule (and not the exception). Hence, a 15 kGy dose of e-beam is expected to provide sterility.

Figure 1D:
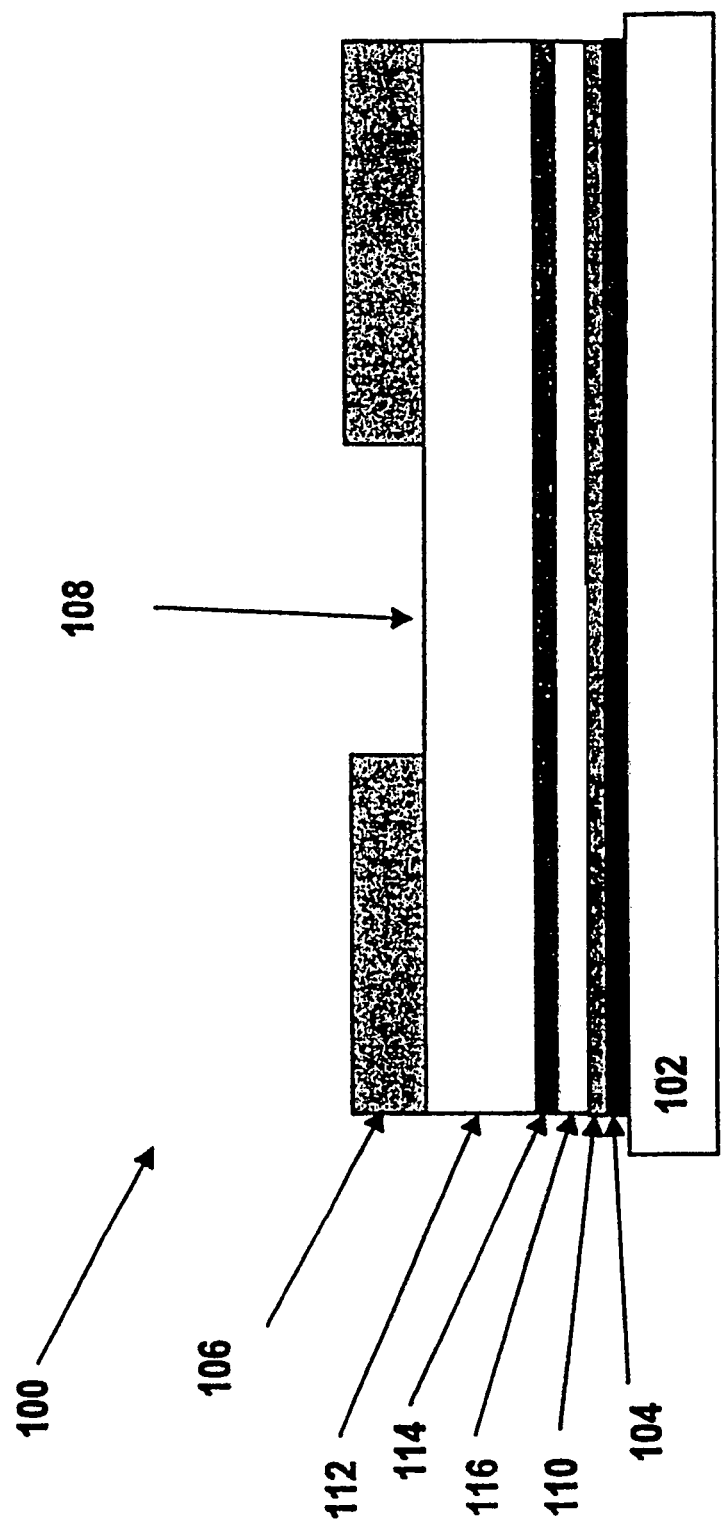
FIG. 1D shows a diagram of shows an alternative sensor design, one comprising an amperometric analyte sensor formed from a plurality of planar layered elements.

Tests of Excipients Useful to Protect Fluorescent Sensors from Radiation Damage:

Experiments were conducted on the fluorescent glucose sensor shown in FIGS. 1A-1C, one comprising MBL and fluorophore compounds (see, e.g. U.S. patent application publication 2008/0188723). Excipients used for protecting the sensor during e-beam sterilization processes were consequently chosen to protect MBL and these fluorophores. Dextran was considered to benefit from the protection applied to MBL. The protective excipients were chosen from the following categories:

Known MBL Binding Sugars:

Binding sugars can protect the carbohydrate recognizing domain (CRD) of the protein, by keeping the peptide structure in the right conformation. However this is not thermodynamically favored compared to non-binding sugars. $\Delta G=\Delta H-T\Delta S$. For binding sugars the $T\Delta S$ contribution is large due to the binding sugar in the CRD being in an ordered conformation instead of the random (non-ordered) water structure in the CRD. The binding sugar will then lower the loss in $\Delta G$ less than a low binding sugar due to entropy effects.

Low-Binding Sugars:

Low-binding sugars can function to provide a more rigid hydrogen-bonding scaffold (compared to water) to support the structure of the protein during radiation.

Antioxidants:

Antioxidants are generally used as protective agents against free radical associated radiation damage. Antioxidants quench radicals by reducing them.

Oxidants:
Oxidants were tested as protective agent for the reduction of the fluorescent dyes. Radicals generated during irradiation could reduce the dyes resulting in bleaching them.

Oxidants could oxidize the dye-radicals formed thus protecting the dyes. Further in this context these compounds were trialed also to show the benefit of using antioxidants.

Amino Acids:
Amino acids are often used to stabilize pharmaceutical formulations. Both hydrophilic and hydrophobic amino acids were tested.

Surfactants:
Surfactants are often used to stabilize pharmaceutical formulations since denaturing often happens at phase transitions or boundaries.

Phenyl Compounds:
Phenyl containing compounds may stabilize the fluorescent dyes via a π-π stacking mechanism (and hence the assay).

Bacteriostats:
Bacteriostat compounds tested were phenyl containing compounds.

In the following experiments, two or more excipients were chosen from each category and tested individually and in combination with ascorbate. For the best excipients in four categories a larger matrix of experiments was trialed.

Results from Screening Round
The list of excipients tested and the concentration of each is shown in Table 1 below.

TABLE 1

A list of tested excipients to protect our sensors during radiation. All excipients were dialyzed into the sensor prior to irradiation. The sensors formulated with oxidative excipients were not de-aerated prior to radiation all other were de-aerated with Ar.

| Excipient Type | Excipients Used | Concentration range tested | Used in combinations[1] |
|---|---|---|---|
| Binding Sugars | Mannose | 1, 2, 5, 10, 20 and 50 mM | Yes |
| | Fructose | 50 mM | No |
| | Melizitose | 20 mM | No |
| Low-Binding Sugars | Sucrose | 100, 500 and 1000 mM | Yes |
| | Trehalose | 500 and 1000 mM | Yes |
| Antioxidants | Ascorbate | 5, 50, 100 and 250 mM | Yes |
| | Nitrite | 5, 10 and 20 mM | Yes |
| | Ureate | 1 and 5 mM | Yes |
| | α-Tocopherol | 1 mg/mL (4.6 mM) | Yes |
| | Nicotinate methylester | 20 and 50 mM | No |
| Oxidants | $H_2O_2$ | 50 mM | Yes |
| | $N_2O$ | Sat'd (gas bubbled through) | No |
| Amino Acids | Lysine | 2 mg/mL | No |
| | Tryptophan | 2 mg/mL | No |
| | Phenylalanine | 2 mg/mL | No |
| Surfactants | Synperonic | 1 mg/mL | No |
| | Tween 20 | 1 mg/mL | No |
| | Tween 80 | 1 mg/mL | No |
| "Drugs" | Acetaminophen | 1, 2, 5, 10 and 20 mM | Yes |
| | Acetylsalicylic acid | 10 mM | Yes |
| | α-Tocopherol | 1 mg/mL (4.6 mM) | Yes |
| Phenyl Containing Compounds | Acetaminophen | 1, 2, 5, 10 and 20 mM | Yes |
| | Acetylsalicylic acid | 10 mM | Yes |
| | α-Tocopherol | 1 mg/mL (4.6 mM) | Yes |
| | Phenol | 1 mg/mL (106 mM) | Yes |
| | m-Cresol | 1 mg/mL (92 mM) | Yes |
| | Tryptophan | 2 mg/mL (98 mM) | Yes |
| | Phenylalanine | 2 mg/mL | No |
| | Nicotinate methylester | 20 and 50 mM | No |
| Bacteriostats | Phenol | 1 mg/mL (106 mM) | Yes |
| | m-Cresol | 1 mg/mL (92 mM) | Yes |
| Combinations | +80 | Max molarity 1M | |

[1] The combination most often used was together with ascorbate.

The excipients listed in Table 1 were evaluated in order to choose which compounds should be used for the test of different combination of excipient. Test endeavored to identify compounds that individually had an expected protective property towards a preferred target (e.g. CRD, Dye, General peptide bond or protein and storage stabilizing effects).

Table 2 provides a brief summary of the results of the screening round. In Table 2, an overview of the excipients tested as protective agents against radiation damages during e-beam (15 kGy dose) is provided. The excipients are listed according to class of compound. Some of the excipients are listed in more than one category.

TABLE 2

| Excipient Type | Excipients | Retention Range (with acc. DR) | Best In Class |
|---|---|---|---|
| Binding Sugars | Mannose | 47%-55% | Mannose |
| | Fructose | | |
| | Melizitose | | |
| Non-Binding Sugars | Sucrose | 47%-90% | Sucrose |
| | Trehalose | | |
| Antioxidants | Ascorbate | 28%-80% | Ascorbate |
| | Nitrite | | |
| | Ureate | | |
| | α-Tocopherol | | |
| | Nicotinate methylester | | |
| Oxidants | $H_2O_2$ | 38%-58% | $N_2O$ |
| | $N_2O$ | | |
| Amino Acids | Lysine | 44%-95%[1] | Tryptophan |
| | Tryptophan | | |
| | Phenylalanine | | |
| Surfactants | Synperonic | 26%-33% | Synperonic |
| | Tween 20 | | |
| | Tween 80 | | |
| "Drugs" | Acetaminophen | 10%-80% | Acetaminophen |
| | Acetylsalicylic acid | | |
| | α-Tocopherol | | |
| Phenyl Containing Compounds | Acetaminophen | 10%-80% | Acetaminophen |
| | Acetylsalicylic acid | | |
| | α-Tocopherol | | |
| | Phenol | | |
| | m-Cresol | | |
| | Tryptophan | | |
| | Phenylalanine | | |
| | Nicotinate methylester | | |
| Bacteriostats | Phenol | 0% | N/A |
| | m-Cresol | | |
| Combinations | +80 | 50-+80% | |

From Table 2 we chose the following four excipients (all best in their excipient class) to be used in combination as follows:

Ascorbate: Used for general protection of the peptide bonds in proteins. In literature mentioned as the best antioxidant and yielding best protection of proteins against free radical attack. However in literature the best protection is obtained with very high concentrations of ascorbate, most often >200 mM which is at least four times the best concentration identified herein. Surprisingly, in tests of the sensor embodiments disclosed herein, it was found that using high concentrations of ascorbate (e.g. 250 mM) yields poor protection while low concentrations of ascorbate (e.g. not more than 100 mM, not more than 50 mM etc.) yields good protection.

Acetaminophen: This compound is not known to interfere with the protein in the assay. However it works as a dynamic and reversible quencher of the fluorescence from AF594. This means that acetaminophen has an effect on the AF594 and could help to protect the dye from radiation damages, e.g. prevent bleaching.

Mannose: Mannose could protect the carbohydrate recognizing domain (CRD) of the protein, by keeping the peptide structure in the right conformation.

Sucrose: Sucrose is often used for building a more rigid hydrogen-bonding scaffold (compared to water) to support the structure of the protein during radiation. Also Sucrose could bring some improved storage stability to the assay.

The list of combinations with the concentration of each excipient and the results are shown in Table 3: Table 3 shows 48 variations over the four chosen excipients that have been tested. The order of the variations is stochastic.

TABLE 3

| Excipient concentration (mM) | | | | Dose response | | |
|---|---|---|---|---|---|---|
| Ascorbate | Aceta-minophen | Mannose | Sucrose | 0 kGy | 15 kGy | Retained[1] |
| 50 | 20 | 5 | | 1.6 | 1.8 | 112.5% |
| 50 | 20 | 5 | 500 | 1.1 | 1.6 | 145.5% |
| *50 | 20 | 1 | | 1.8 | 2.1 | 116.7% |
| 50 | 20 | 1 | 100 | 2.2 | 1.9 | 86.4% |
| *50 | 20 | 1 | 500 | 1.5 | 2.1 | 140.0% |
| 50 | 10 | 5 | | 1.8 | 1.7 | 94.4% |
| 50 | 10 | 5 | 100 | 1.5 | 1.8 | 120.0% |
| 50 | 10 | 5 | 500 | 2.0 | 1.6 | 80.0% |
| 50 | 10 | 1 | | 1.5 | 1.0 | 66.7% |
| 50 | 10 | 1 | 100 | 1.8 | 1.4 | 77.8% |
| 50 | 10 | 1 | 500 | 1.7 | 1.0 | 58.8% |
| 50 | 10 | | | 1.9 | 1.7 | 89.5% |
| 50 | 5 | 5 | | 0.8 | 1.7 | 212.5% |
| 50 | 2 | | | 2.0 | 1.1 | 55.0% |
| 50 | | 5 | | 2.1 | 1.7 | 81.0% |
| 50 | | 5 | 100 | 1.9 | 1.4 | 73.7% |
| 50 | | 5 | 500 | 1.7 | 1.8 | 105.9% |
| 50 | | 1 | | 1.8 | 1.7 | 94.4% |
| 50 | | 1 | 100 | 1.7 | 1.5 | 88.2% |
| 50 | | 1 | 500 | 1.8 | 1.8 | 100.0% |
| 50 | | | 1000 | 2.3 | 1.8 | 78.3% |
| 20 | 10 | | | 2.0 | 1.7 | 85.0% |
| 10 | 20 | 5 | | 1.6 | 1.0 | 62.5% |
| 10 | 20 | 5 | 100 | 0.8 | 0.8 | 100.0% |
| 10 | 20 | 5 | 500 | 2.2 | 1.2 | 54.5% |
| 10 | 20 | 1 | | 1.9 | 1.9 | 100.0% |
| 10 | 20 | 1 | 100 | 0.9 | 0.8 | 88.9% |
| 10 | 20 | 1 | 500 | 2.1 | 1.7 | 81.0% |
| 10 | 10 | 5 | | 1.3 | 1.5 | 115.4% |
| 10 | 10 | 5 | 100 | 1.6 | 1.7 | 106.3% |
| 10 | 10 | 5 | 500 | 1.7 | 1.6 | 94.1% |
| 10 | 10 | 1 | | 1.7 | 1.5 | 88.2% |
| 10 | 10 | 1 | 100 | 1.7 | 1.0 | 58.8% |
| 10 | 10 | 1 | 500 | 2.0 | 1.9 | 95.0% |
| 10 | 5 | 5 | | 1.9 | 1.3 | 68.4% |
| 10 | 2 | | | 1.8 | 1.0 | 55.6% |
| 10 | | 5 | 100 | 1.8 | 1.6 | 88.9% |
| 10 | | 1 | | 1.0 | 0.0 | 0.0% |
| 10 | | 1 | 100 | 1.8 | 1.5 | 83.3% |
| 5 | 2 | | | 1.8 | 1.2 | 66.7% |

TABLE 3-continued

| Excipient concentration (mM) | | | | Dose response | | |
|---|---|---|---|---|---|---|
| Ascorbate | Aceta-minophen | Mannose | Sucrose | 0 kGy | 15 kGy | Retained[1] |
| 5 | | | 1000 | 2.3 | 1.8 | 78.3% |
| | 20 | | | 2.2 | 1.7 | 77.3% |
| | 10 | | | 2.0 | 1.6 | 80.0% |
| | 5 | | | 2.2 | 1.6 | 72.7% |
| | 2 | | | 2.3 | 1.5 | 63.0% |
| | 1 | | | 2.4 | 1.3 | 54.2% |
| | | | 100 | 2.8 | 1.7 | 60.7% |
| | | | 500 | 1.8 | 1.9 | 105.6% |

Figure 3:
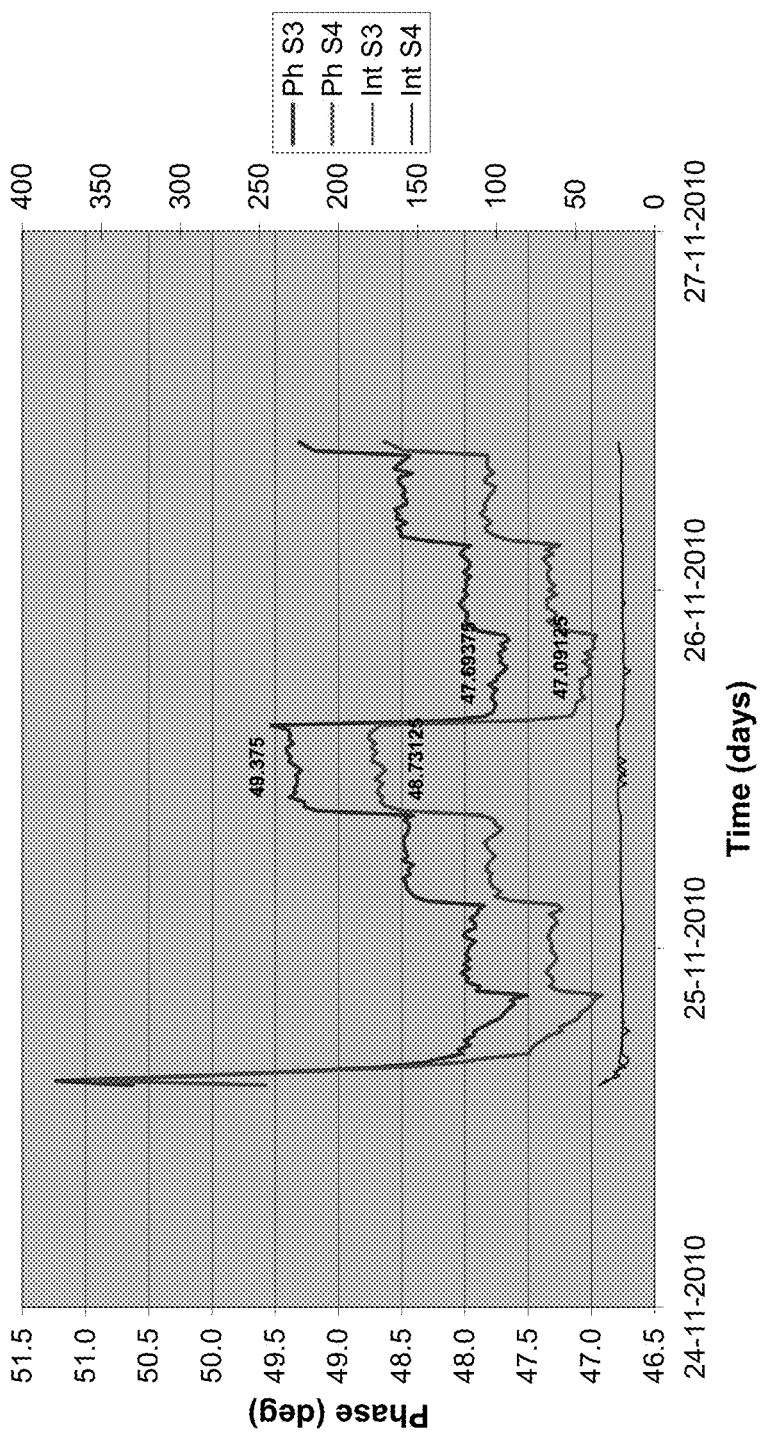
FIG. 3 shows a plot of phase and intensity data obtained from sensors after exposure to 15 kGy of radiation. The dose response is 1.7 after radiation compared to 2.1 before i.e. a retention of 81%.

[1]Retained DR > 100% should not be possible but if the 0 kGy DR is unexpected low retained DR can become > 100%
*High absolute DR after radiation The plot of data shown in FIG. 3 from the SITS system shows a test run of a set of sensors that has had good protection during radiation. FIG. 3 shows a plot of phase and intensity data obtained from sensors after exposure to 15 kGy of radiation. The dose response is 1.7 after radiation compared to 2.1 before i.e. a retention of 81%. Note the long equilibration time of the sensor after startup. This most likely origins from the large concentration of sucrose used in the formulation. As is known in the art, concentrations of agents in aqueous solutions can be easily changed via processes such as dialysis.

Excipients Individual Effects

Figure 4:
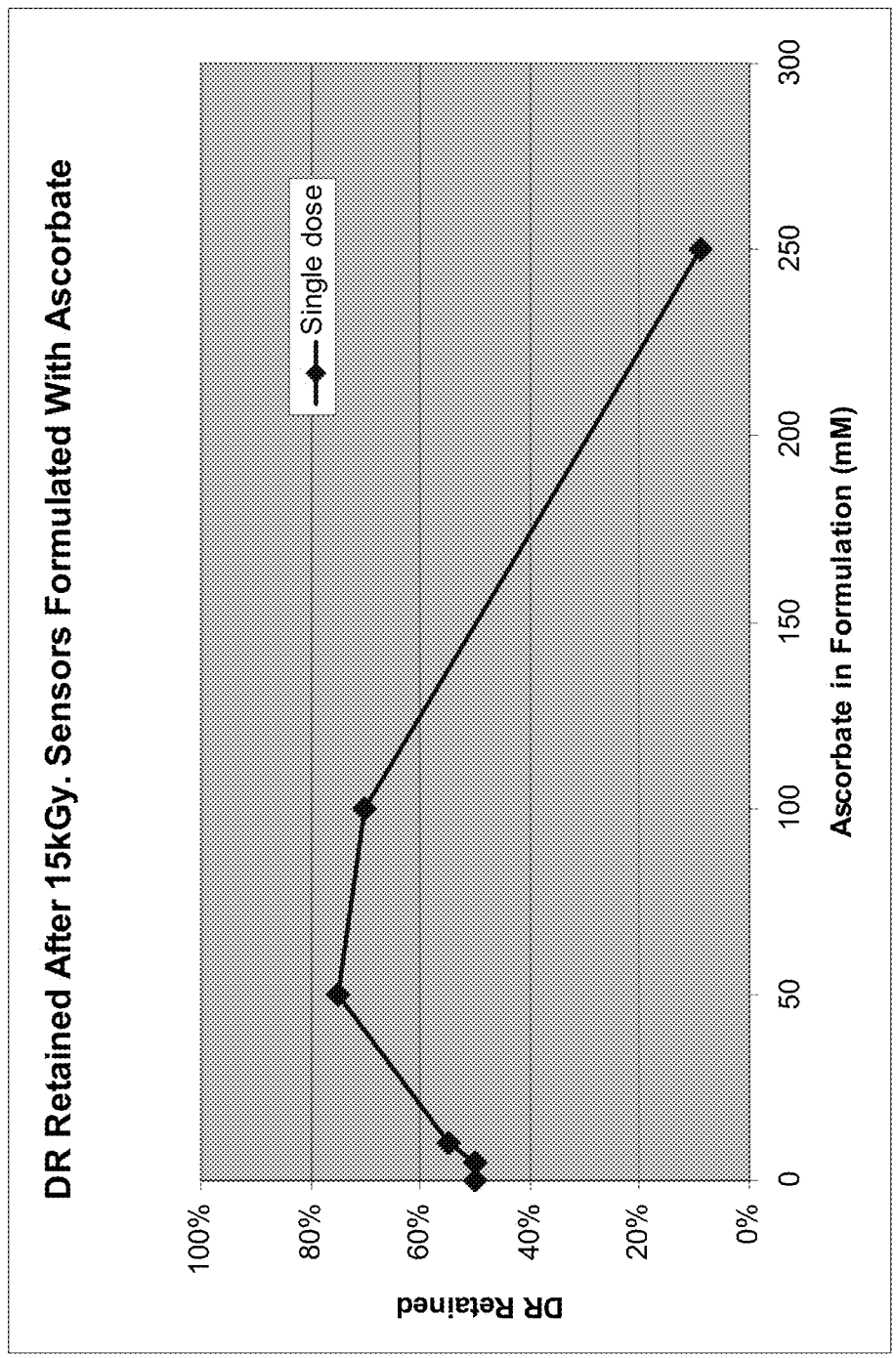
FIG. 4 shows a graph of data on DR retained for irradiated sensors as a function of Ascorbate concentration used for formulation. Too low or too high concentrations of Ascorbate used both yield low retained DR whereas the 20 mM to 100 mM concentration range yields good protection.

In order to get an overview of the effect of the individual excipients the results will be visualized as seen FIG. 4. FIG. 4 shows a graph of data on DR retained for irradiated sensors as a function of Ascorbate concentration used for formulation. Too low or too high concentrations of Ascorbate used both yield low retained DR whereas the 20 mM to 100 mM concentration range yields good protection.

Figure 5:
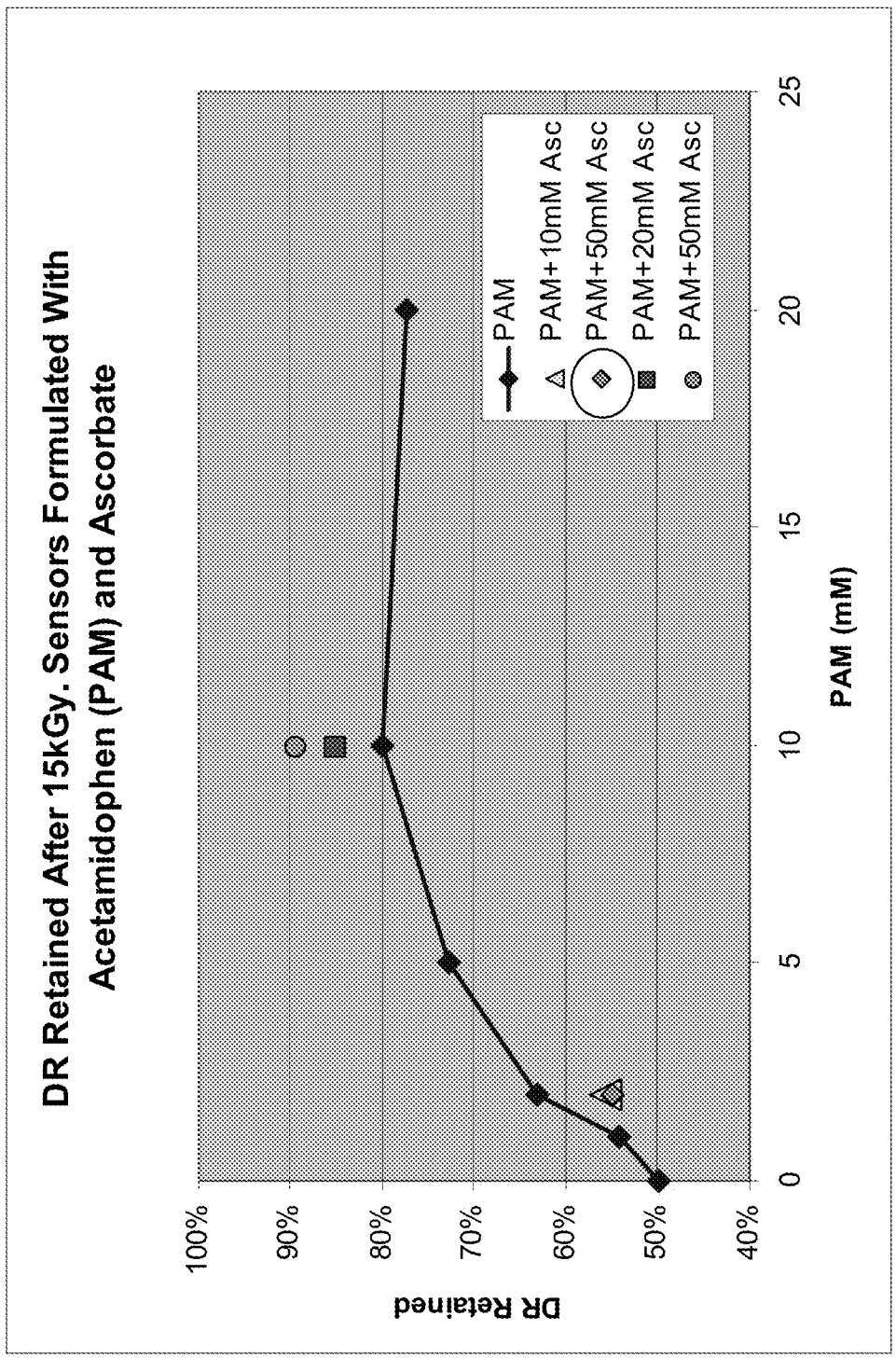
FIG. 5 shows a graph of data on DR retained for irradiated sensors as a function of Acetaminophen (=paracetamol, hence abbreviated PAM) concentration used for formulation. It is seen that using low concentrations of Acetaminophen yields low retained DR whereas the use of concentrations above 10 mM yields good protection. Further it is shown that adding Ascorbate to the excipients in most cases provides better protective effects.

FIG. 5 shows a graph of data on DR retained for irradiated sensors as a function of Acetaminophen (=paracetamol, hence abbreviated PAM) concentration used for formulation. It is seen that using low concentrations of Acetaminophen yields low retained DR whereas the use of concentrations above 10 mM yields good protection. Further it is shown that adding Ascorbate to the excipients in most cases gives better protection.

Figure 6:
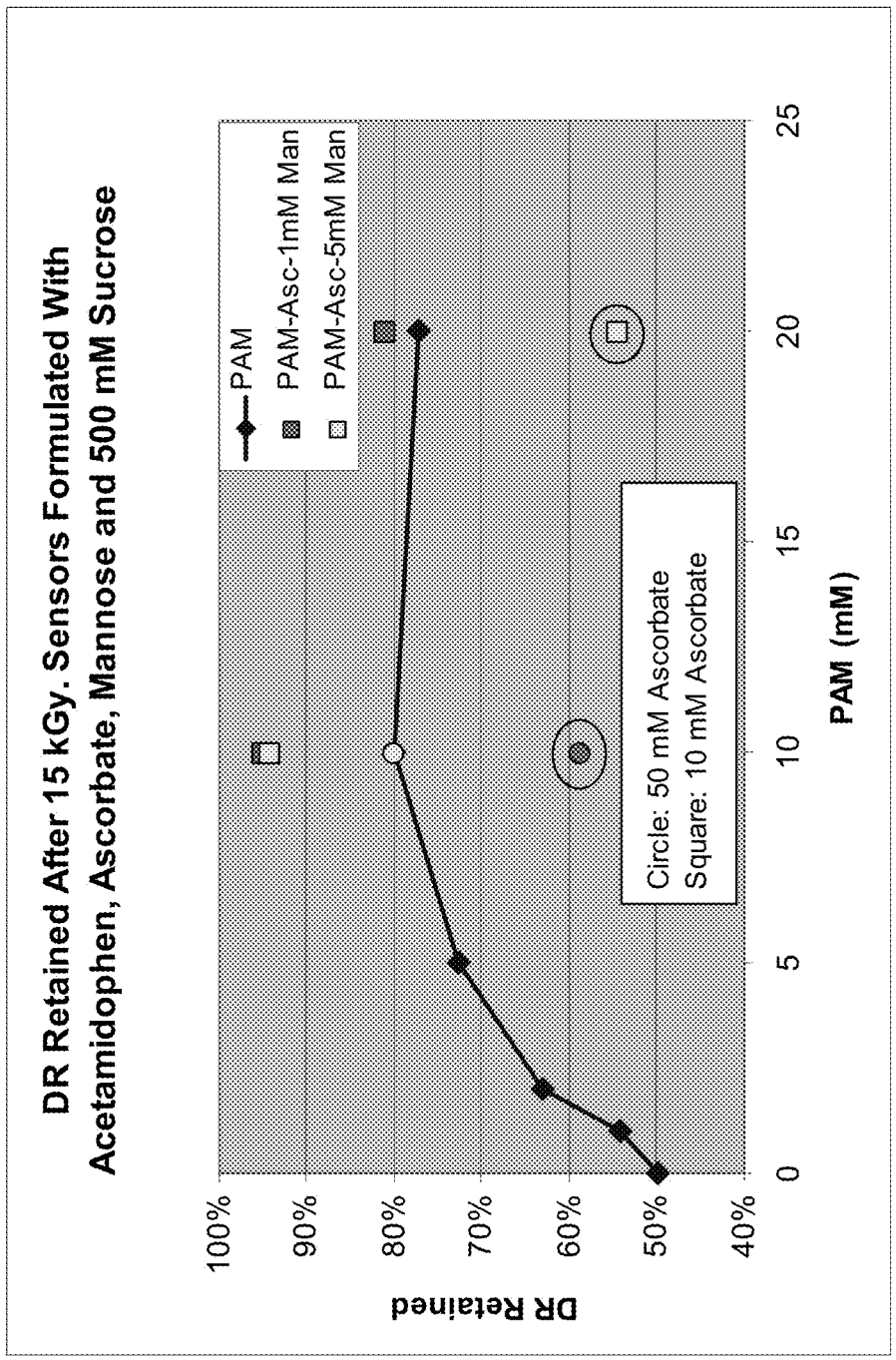
FIG. 6 shows a graph of data on DR retained for irradiated sensors as a function of Acetaminophen concentration used for formulation.

FIG. 6 shows data of DR retained for irradiated sensors as a function of Acetaminophen concentration used for formulation.

Figure 7:
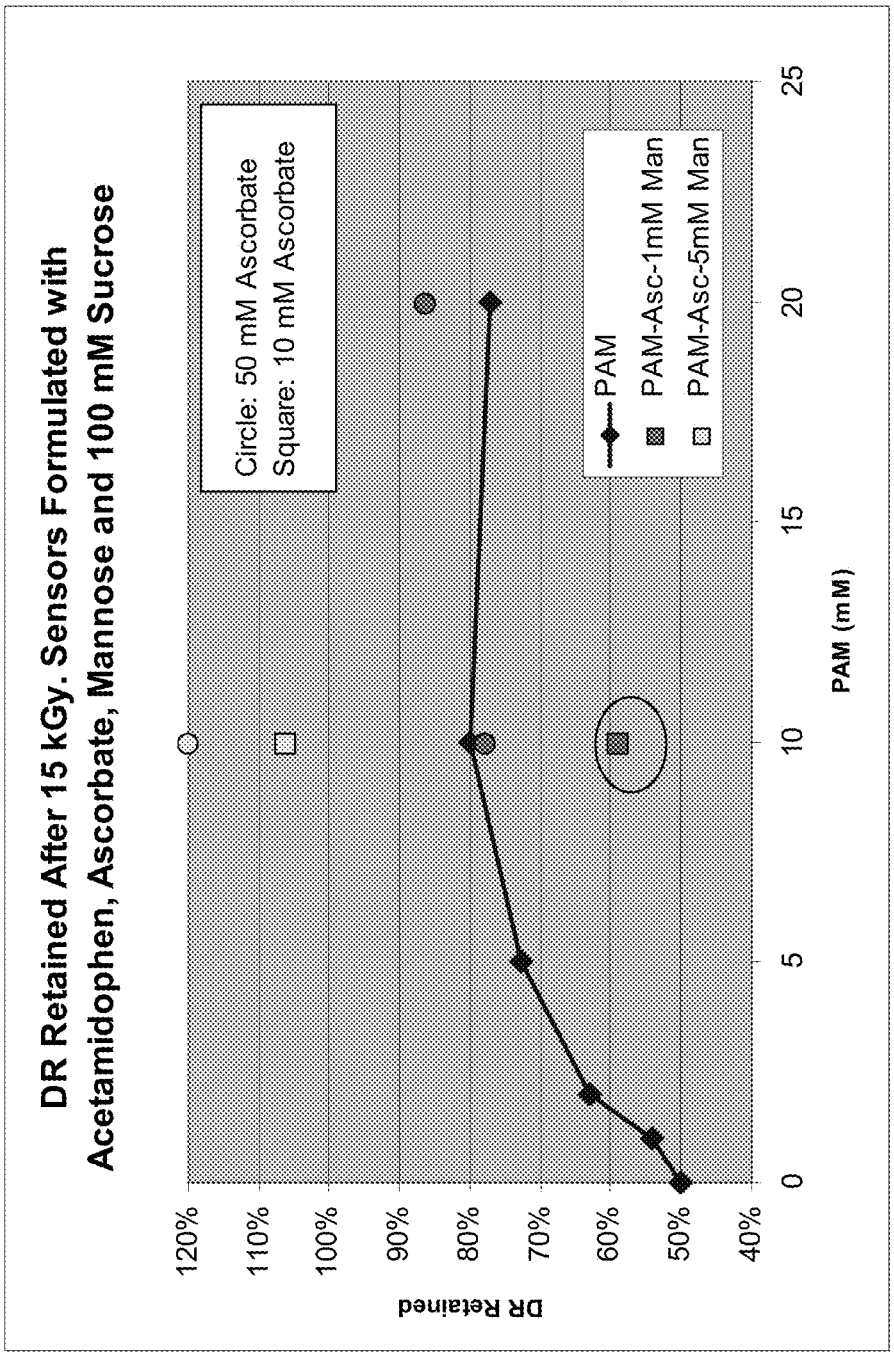
FIG. 7 shows a graph of data of DR retained for irradiated sensors as a function of Acetaminophen concentration used for formulation. All sensors have contained 100 mM Sucrose and variation of additions of Ascorbate and Mannose are also shown.

FIG. 7 shows data of DR retained for irradiated sensors as a function of Acetaminophen concentration used for formulation. All sensors have contained 100 mM Sucrose and variation of additions of Ascorbate and Mannose are also shown.

Figure 8:
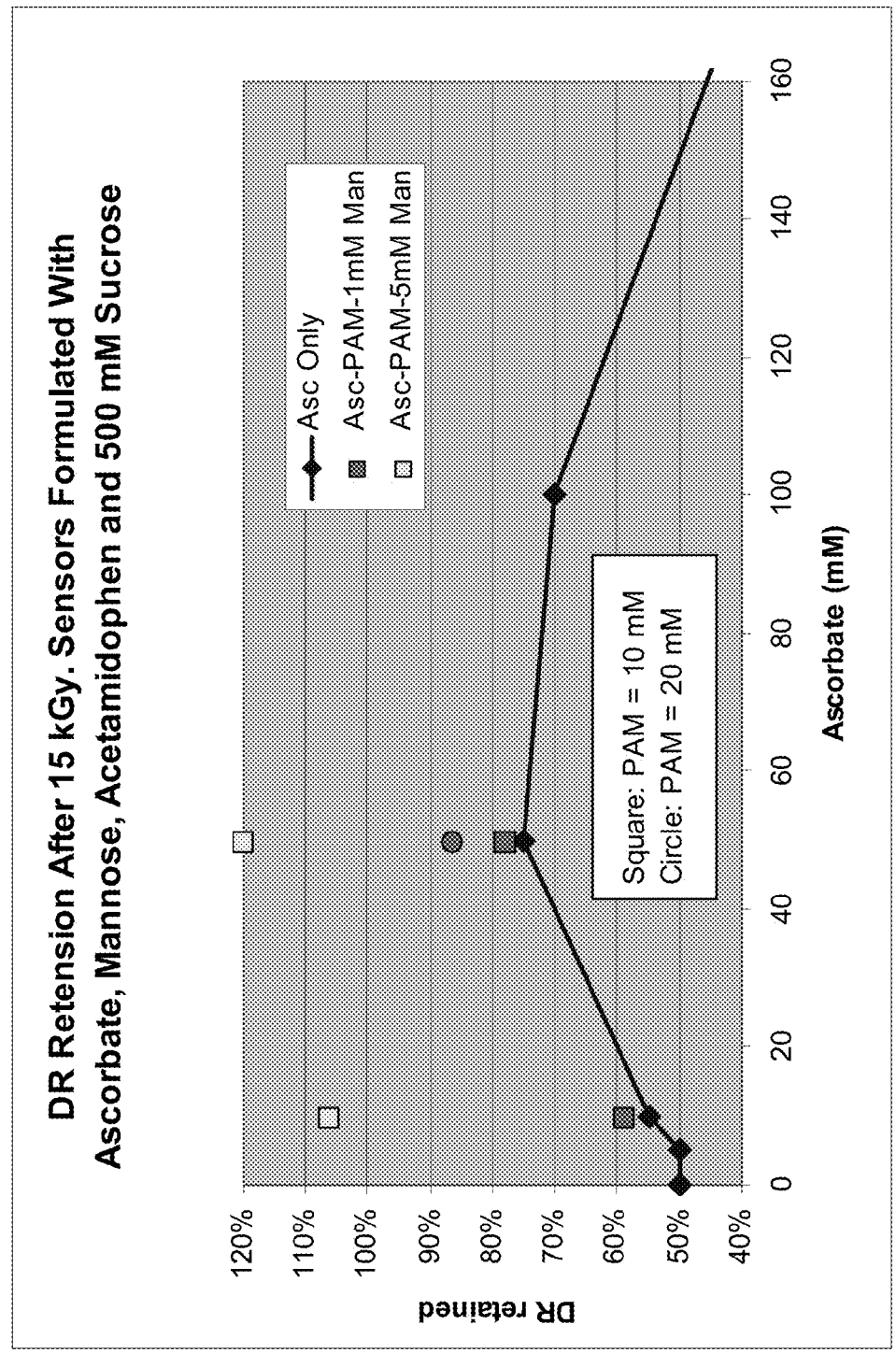
FIG. 8 shows a graph of data of DR retained for irradiated sensors as a function of Ascorbate concentration used for formulation. All sensors have contained 500 mM Sucrose and variation of additions of Acetaminophen (PAM) and Mannose are also shown.

FIG. 8 shows data of DR retained for irradiated sensors as a function of Ascorbate concentration used for formulation. All sensors have contained 500 mM Sucrose and variation of additions of Acetaminophen (PAM) and Mannose are also shown.

Figure 9:
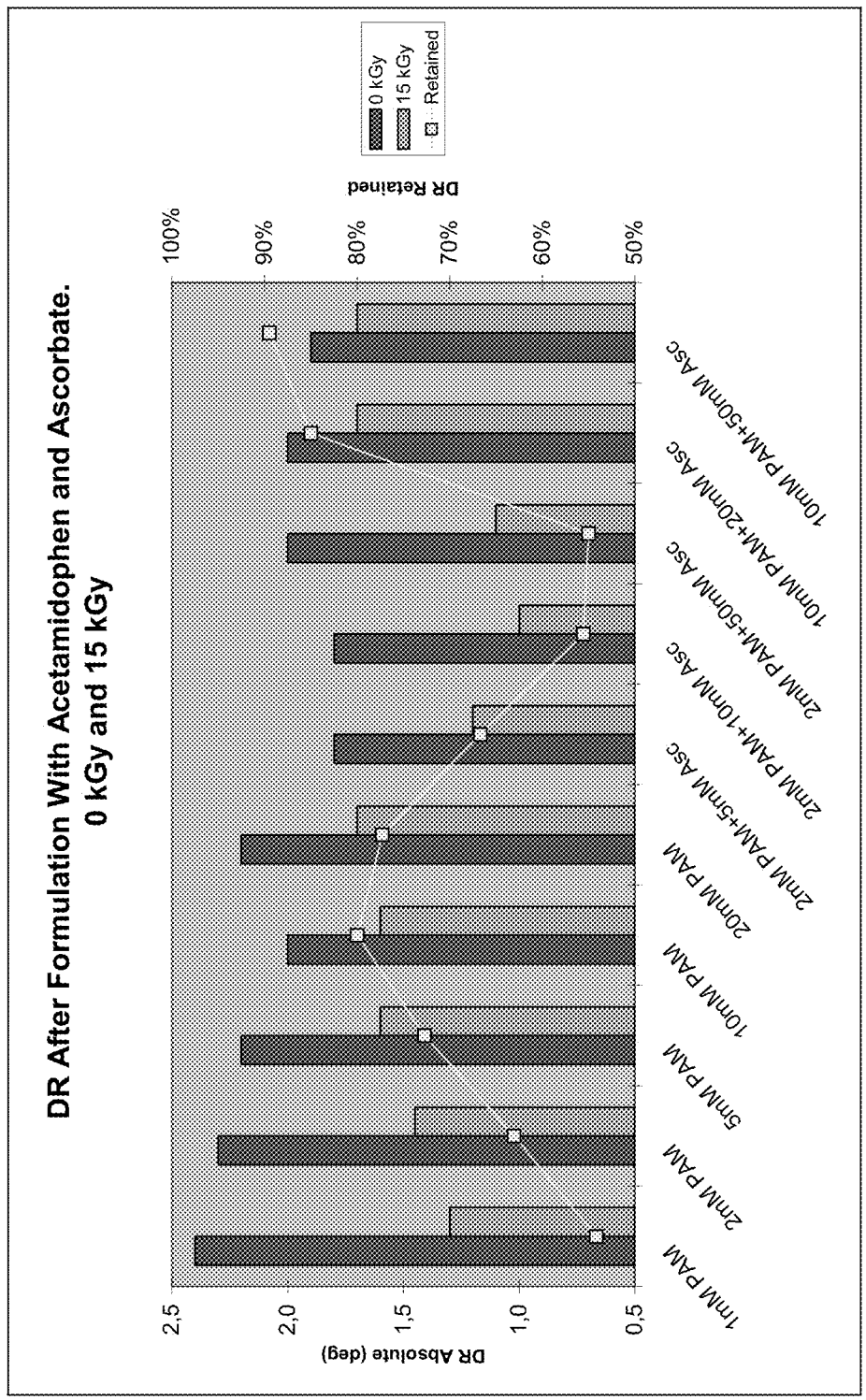
FIG. 9 shows a bar graph of data presenting the absolute DR for both radiated and non-radiated sensor as a function of formulating the sensors with Acetaminophen and Ascorbic acid/ascorbate.

FIG. 9 shows a bar graph of data presenting the absolute DR for both radiated and non-radiated sensor as a function of formulating the sensors with Acetaminophen and Ascorbic acid.

Figure 10:
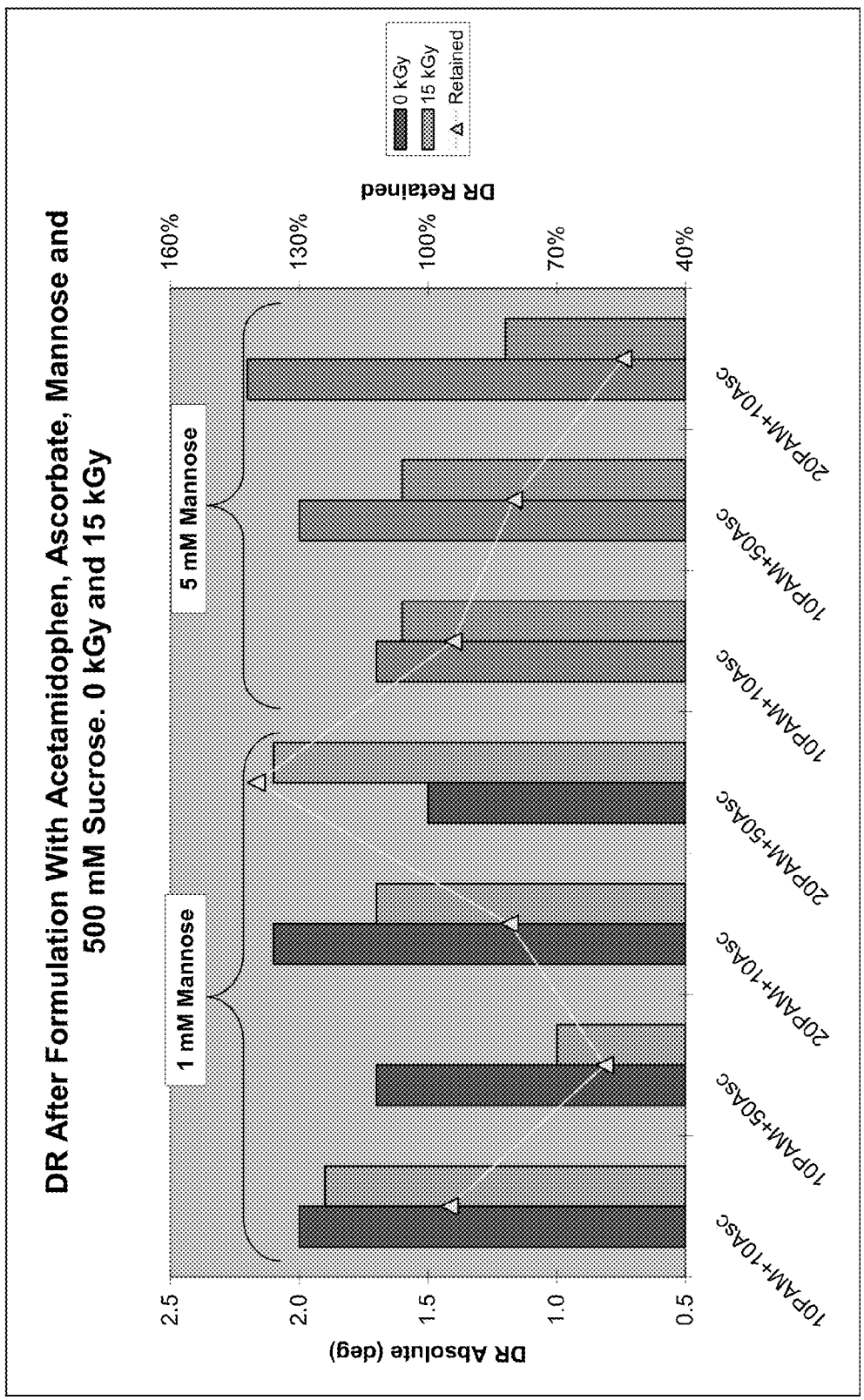
FIG. 10 shows a bar graph of data presenting the absolute DR for both radiated and non-radiated sensor as a function of formulating the sensors with Acetaminophen, Ascorbic acid, Mannose and 500 mM Sucrose. The overall result is illustrated in FIG. 11.

FIG. 10 shows a bar graph of data presenting the absolute DR for both radiated and non-radiated sensor as a function of formulating the sensors with Acetaminophen, Ascorbic acid, Mannose and 500 mM Sucrose. An overall result is illustrated in FIG. 11.

Figure 11:
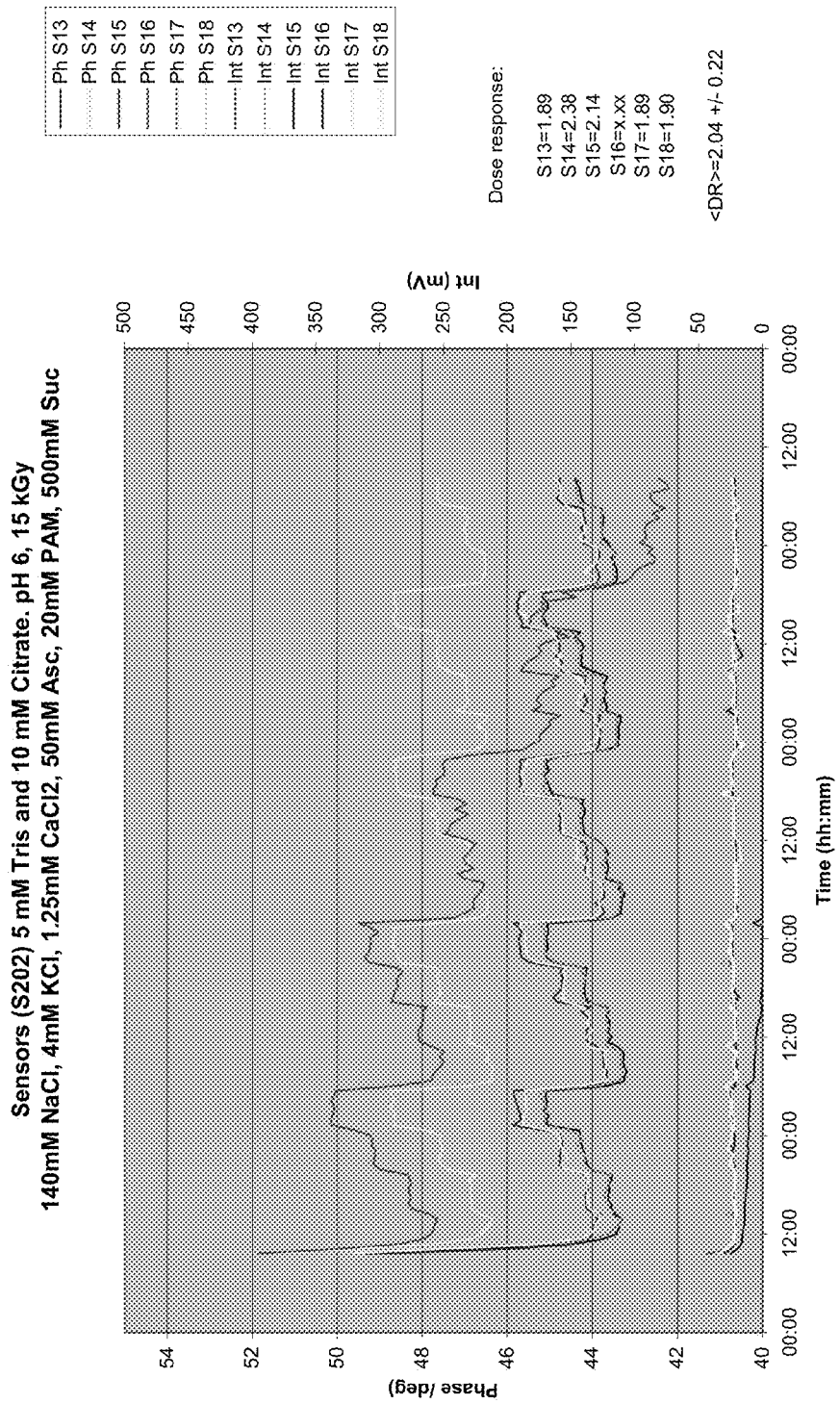
FIG. 11 shows a graph of data showing sensor response after using Tris/Citrate saline buffer+excipients. Sensors show good retention of DR.

FIG. 11 shows a graph of data showing sensor response after using Tris/Citrate saline buffer+excipients. Sensors show good retention of DR.

Figure 12:
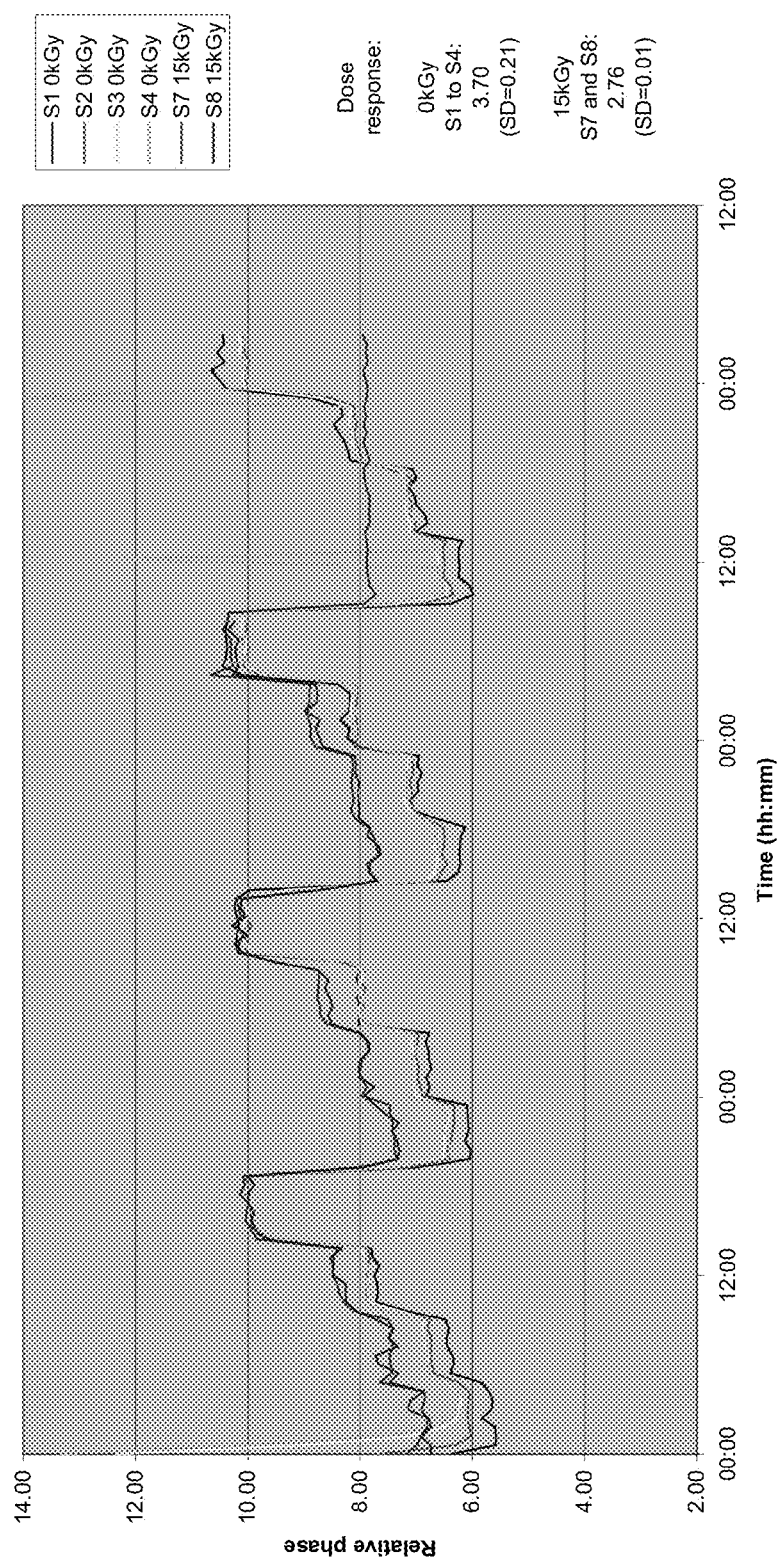
FIG. 12 shows a graph of data presenting a direct comparison of e-beamed and non e-beamed sensors.
Figure 13:
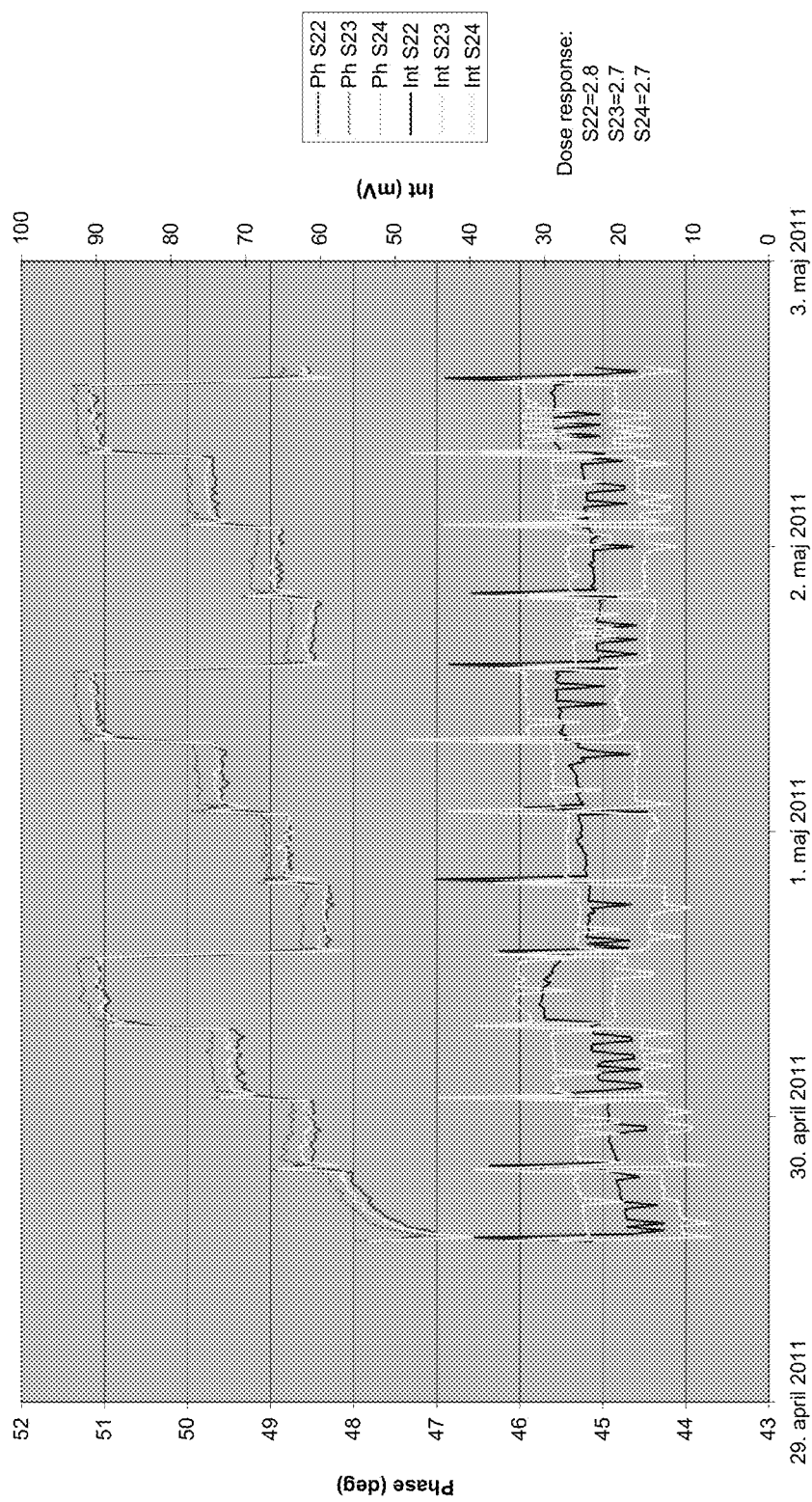
FIG. 13 shows a graph of data obtained from a native sensor tested after storage in PBS pH=5.5. The sensor itself has no problem with the PBS buffer.

FIG. 12 shows a graph of data presenting a direct comparison of e-beamed and non e-beamed sensors.
Buffer Impact on the Sensor Dose Response Retentions after e-Beam Due to a demand for not degrading the polymer used on the sensor pH level needs to be around 6 during wet storage.
PBS Buffer Results FIG. 13 shows a graph of data obtained from a native sensor tested after storage in PBS pH=5.5. The sensor itself has no problem with the PBS buffer.

Figure 14:
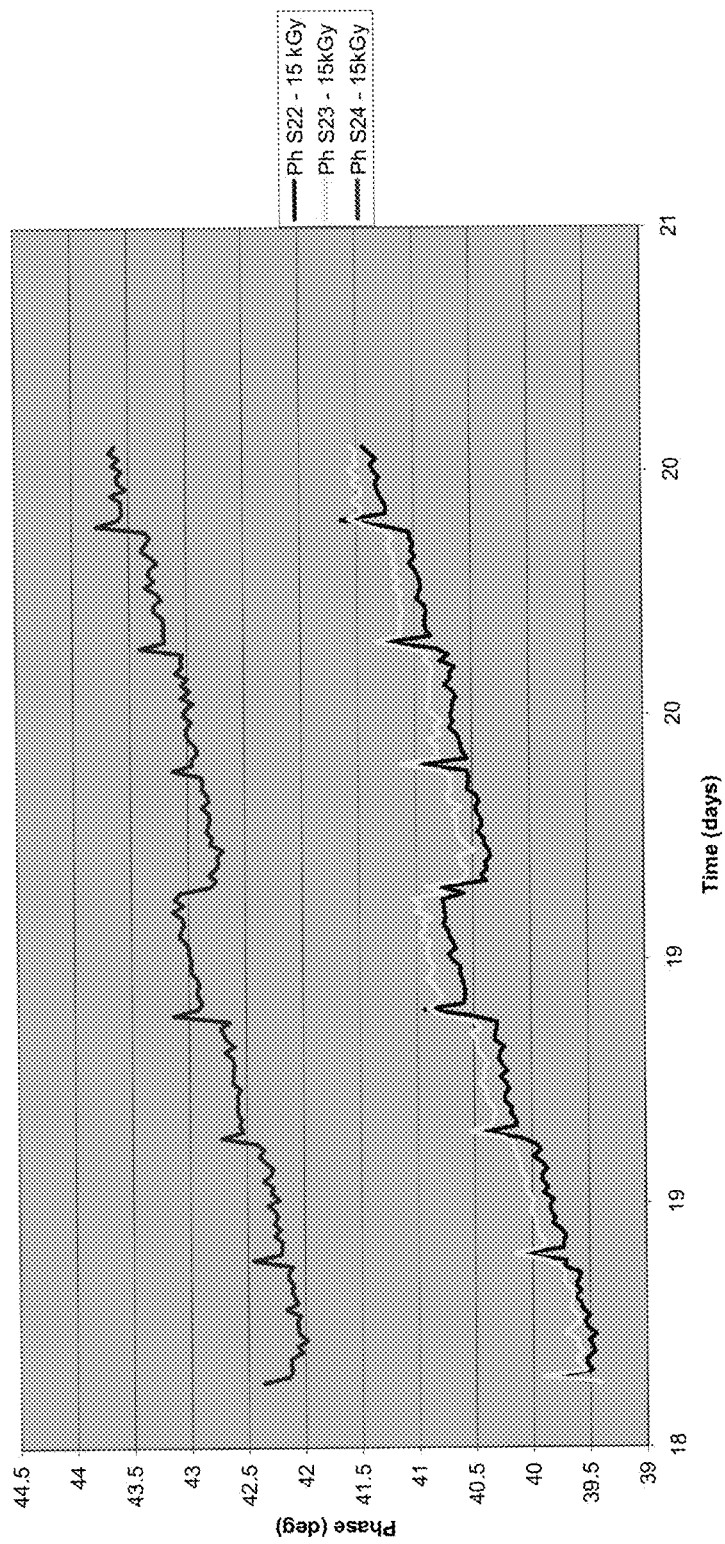
FIG. 14 shows a graph of data obtained from a sensor with excipients added (500 mM sucrose, 20 mM Acetaminophen and 50 mM Ascorbate) in PBS buffer during e-beam irradiation.

FIG. 14 shows a graph of data obtained from a sensor with excipients added (500 mM sucrose, 20 mM Acetaminophen and 50 mM Ascorbate) in PBS buffer during e-beam.

Figure 15:
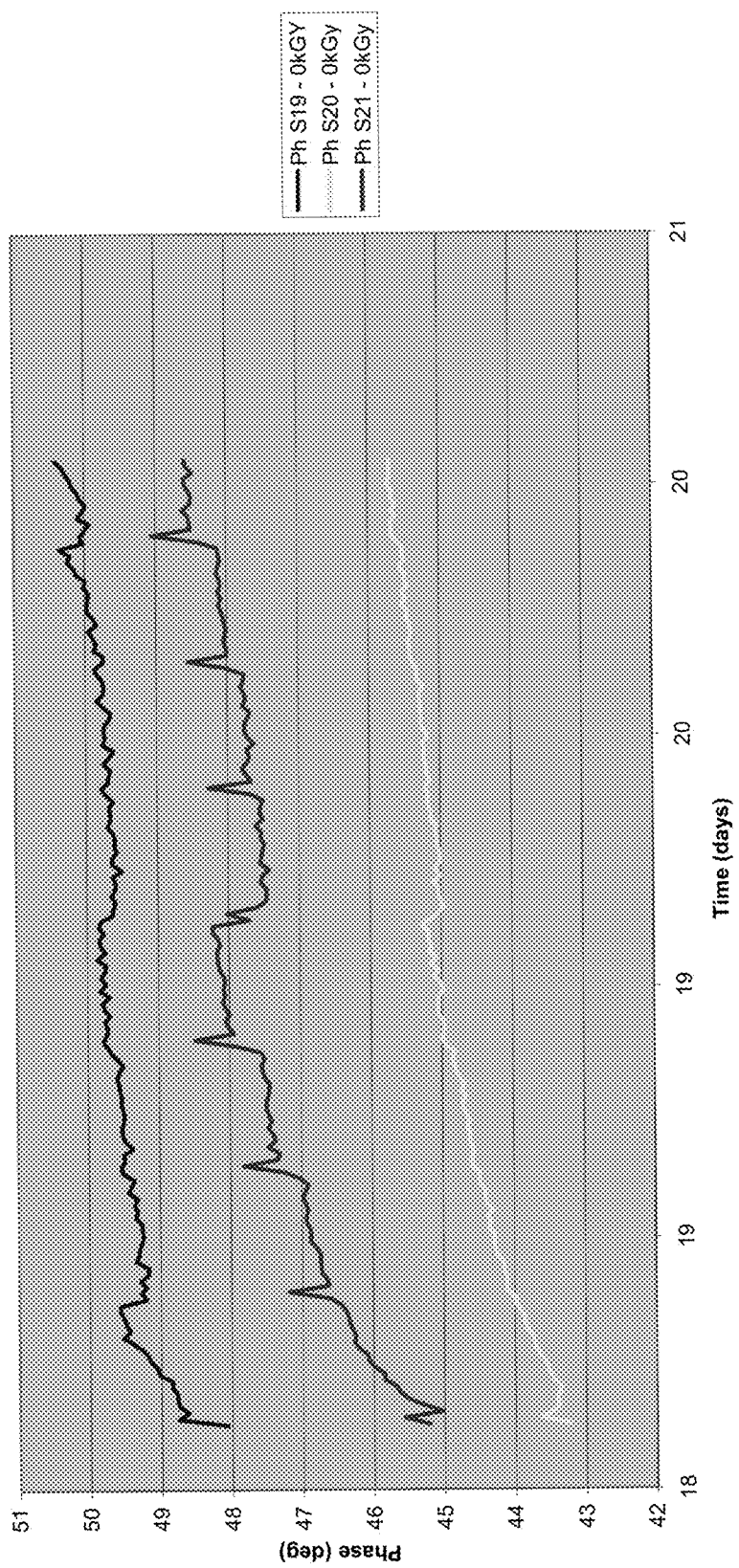
FIG. 15 shows a graph of data obtained from a sensor with excipients added (500 mM sucrose, 20 mM Acetaminophen and 50 mM Ascorbate) in PBS buffer.

FIG. 15 shows a graph of data obtained from a sensor with excipients added (500 mM sucrose, 20 mM Acetaminophen and 50 mM Ascorbate) in PBS buffer. No dose response and large drift is observed even though the sensors have not been e-beamed.
Alternative Buffers Alternative clinically acceptable buffers are shown in Table 4.

TABLE 4

List of optional buffers in the desired range together with their redox state.

| Buffer | pK1 | pK2 | pK3 | Primary amine | "Red-Ox State" | Comment |
| --- | --- | --- | --- | --- | --- | --- |
| Phosphoric Acid | 2.15 | 7.20 | 12.33 | No | P = +7 | +Excipients DR Loss |
| Glycine | 2.35 | 9.78 | | Yes | C = +3 | |
| Alanine | 2.71 | 9.10 | | Yes | C = +3 | |
| Tartaric Acid | 3.04 | 4.37 | | No | C = +3 | |
| Citrate | 3.13 | 4.76 | 6.40 | No | C = +3 | |
| Lactate | 3.86 | | | No | C = +3 | |
| Ascorbic Acid | 4.17 | 11.57 | | No | C = +2 | |
| Acetic Acid | 4.76 | | | No | C = +3 | |
| Uric Acid | 5.83 | | | No | | Solubility problem |
| Carbonic acid/Bicarbonate | 6.35 | 10.33 | | No | C = +4 | $CO_2$ pressure to keep pH |
| Tris | 8.06 | | | Yes | | |

Figure 16:
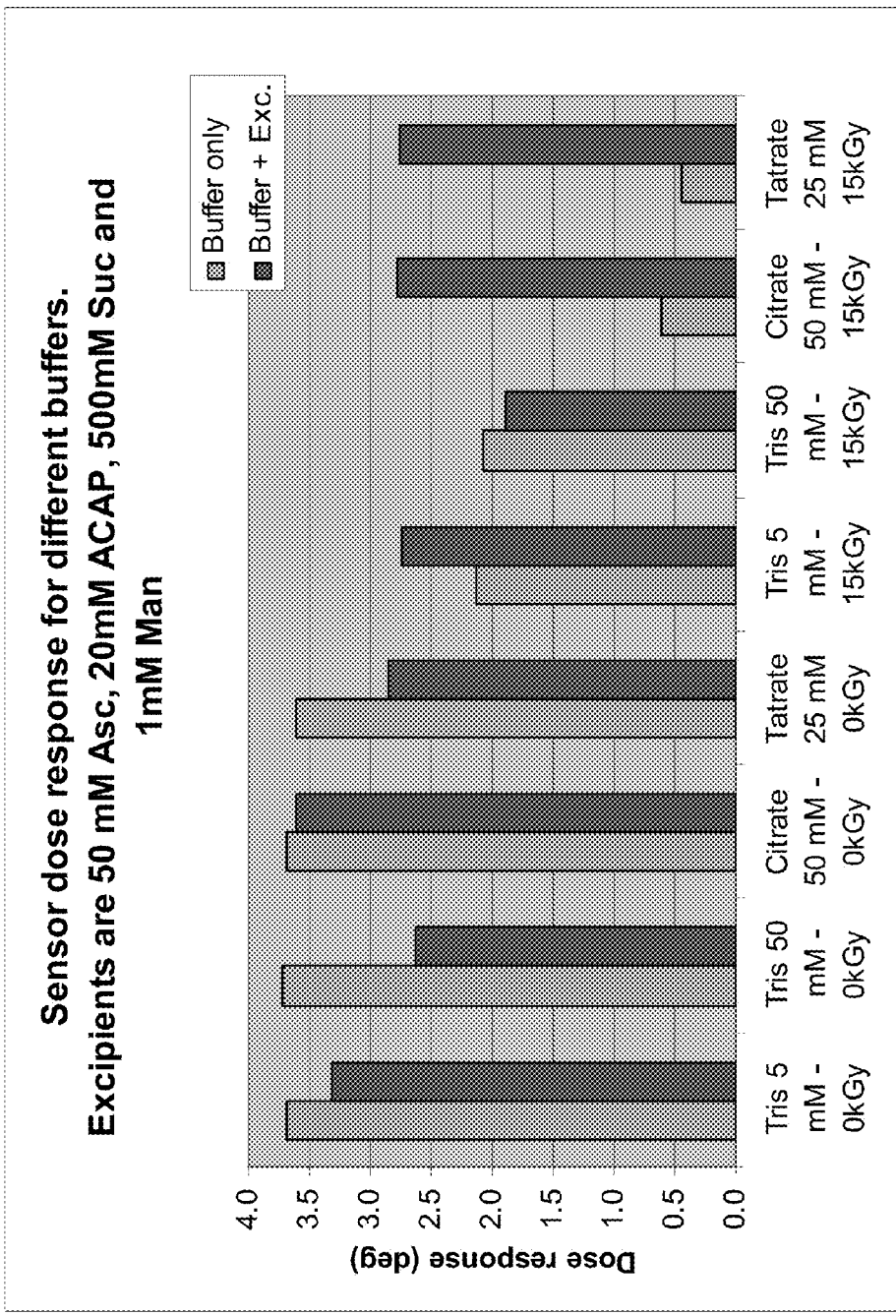
FIG. 16 shows a bar graph of data on retained DR for using different buffer concentrations.

Citrate was found to be superior, and tested in up to 50 mM concentration. Citrate works OK alone but better if Tris is added:

FIG. 16 shows a bar graph of data on retained DR for using different buffer concentrations.

Figure 17:
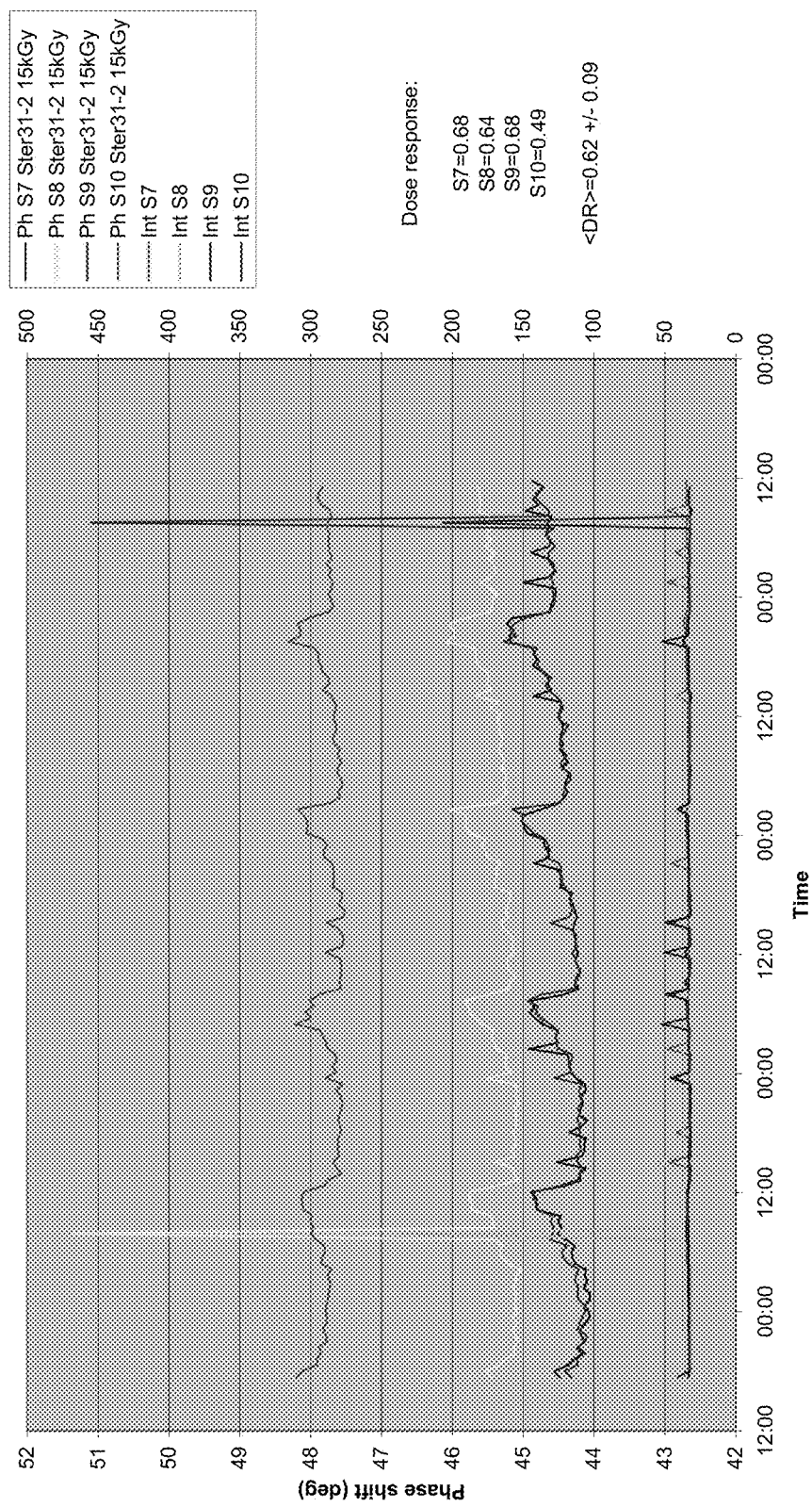
FIG. 17 shows a graph of data resulting from sensors using citrate only during e-beam irradiation.

FIG. 17 shows a graph of data resulting from sensors using citrate only during e-beam irradiation.

Figure 18:
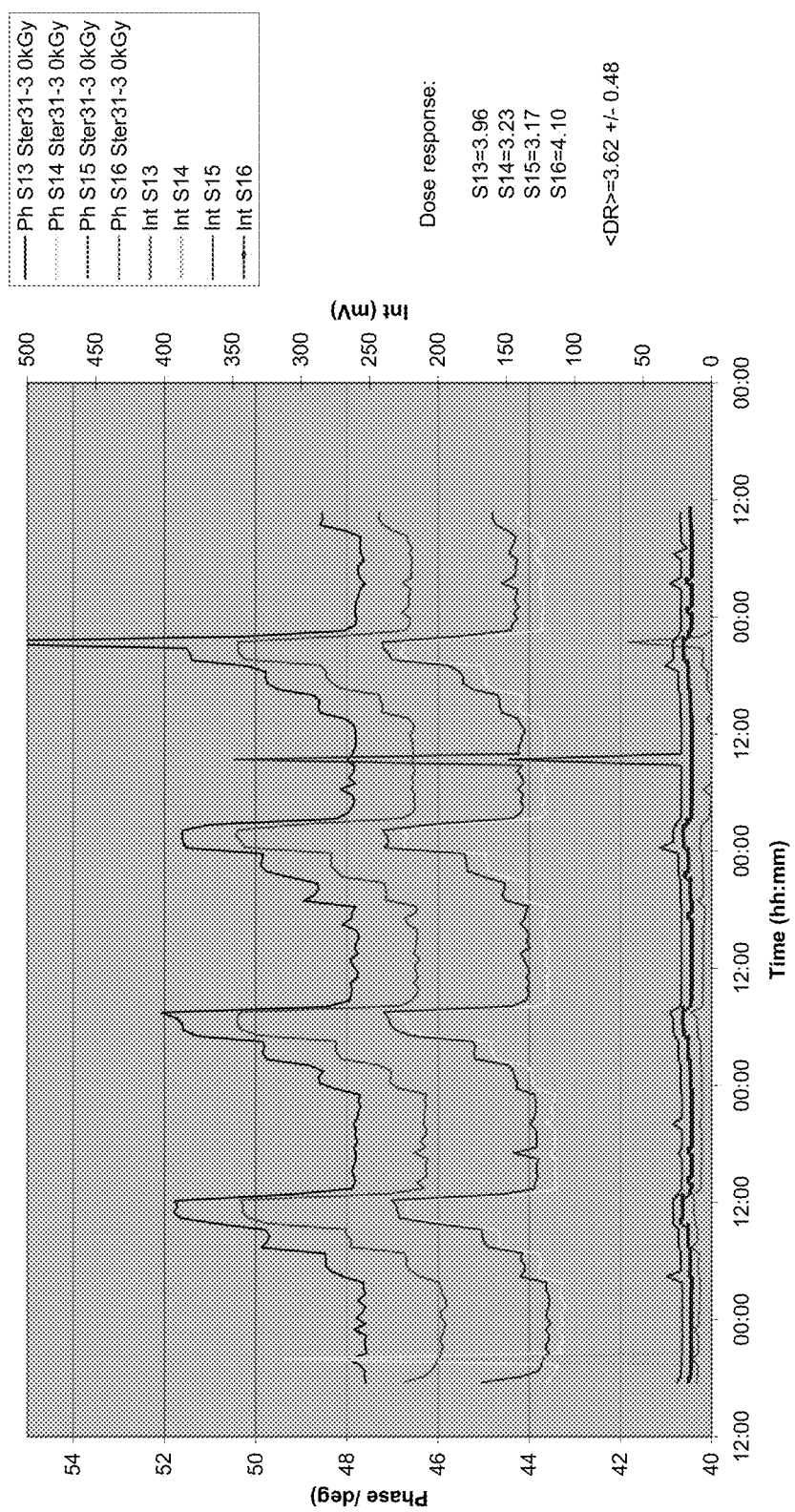
FIG. 18 shows a graph of data resulting from sensors using citrate and excipients during e-beam irradiation.

FIG. 18 shows a graph of data resulting from sensors using citrate and excipients during e-beam irradiation.
Amines to Protect the Chemistry from e-Beam Damages In certain embodiments, amines can be included in the formulations (e.g. as a good quencher of radicals). Experimental results have shown that Tris (primary amine) by itself provides protection and that this protective effect is improved when excipients are added. Illustrative amines include urea, creatine, creatin, as well as the 20 naturally occurring amino acids.

The data in this Example confirms that the effects of a single excipient as well as the effects of combinations of excipients on glucose sensor DR retention following radiation sterilization are unpredictable. In these experiments, categories of agents tested included surfactants, amino acids (hydrophilic/hydrophobic), sugars (binding/non-binding), oxidants, antioxidants, drugs, bacteriostats, and combinations of these agents. The "best-in-class" excipients appear to include ascorbate, mannose, sucrose (high concentration) and acetaminophen (low concentration). The experimental data provides evidence that combinations of excipients can protect different specific sites or functionalities of a sensor against radiation damages. Ascorbate, mannose, sucrose and acetaminophen in combination provide particularly good signal retention for sensors. Typical embodiments of the invention include a combination of two to four excipients from each group and using a combination buffer consisting of 5 mM Tris and/or 10 mM Citrate saline buffer. Some embodiments include sensor storage stability enhancing agents such as low-binding sugars (sucrose, trehalose and other polyols)

The invention claimed is:

1. A method of inhibiting damage to a saccharide sensor that can result from a radiation sterilization process, the method comprising combining the saccharide sensor with an aqueous radioprotectant formulation during the sterilization process, wherein:
    the saccharide sensor comprises a saccharide binding polypeptide having a carbohydrate recognition domain;
    the aqueous radioprotectant formulation comprises a saccharide selected for its ability to bind the saccharide binding polypeptide; and
    performing the sterilization process under conditions selected so that the saccharide binds the saccharide binding polypeptide, thereby inhibiting damage to the saccharide sensor that can result from the radiation sterilization process.

2. The method of claim 1, wherein the saccharide binding polypeptide comprises mannan binding lectin, concanavalin A or glucose oxidase.

3. The method of claim 1, wherein the saccharide comprises glucose, mannose, fructose, melizitose, N-acetyl-D-glucosamine, sucrose or trehalose.

4. The method of claim 1, wherein the aqueous radioprotectant formulation comprises an antioxidant selected from the group consisting of ascorbate, urate, nitrite, vitamin E, α-tocopherol or nicotinate methylester.

5. The method of claim 1, wherein:
    the saccharide sensor comprises a fluorophore; and
    the aqueous radioprotectant formulation comprises a fluorophore quenching composition selected for its ability to quench the fluorophore.

6. The method of claim 1, wherein the aqueous radioprotectant formulation comprises a buffering agent.

7. The method of claim 6, wherein the buffering agent is selected from the group consisting of citrate, tris(hydroxymethyl)aminomethane (TRIS) and tartrate.

8. The method of claim 1, wherein the radiation sterilization process comprises a single dose of radiation.

9. The method of claim 1, wherein the radiation sterilization process comprises electron beam irradiation.

10. A composition of matter comprising:
    a saccharide sensor comprising:
        a saccharide binding polypeptide having a carbohydrate recognition domain; and
        a fluorophore; and
    an aqueous radioprotectant formulation comprising:
        a saccharide, wherein the saccharide is bound to the carbohydrate recognition domain;
        an antioxidant compound, wherein the antioxidant compound is selected from the group consisting of ascorbate, urate, nitrite, vitamin E, α-tocopherol or nicotinate methylester; and
        a fluorophore quenching composition.

11. The composition of claim 10, wherein the fluorophore quenching composition comprises acetaminophen.

12. The composition of claim 11, wherein the aqueous radioprotectant formulation comprises acetaminophen in a concentration of at least 1 mM to 50 mM.

13. The composition of claim 10, wherein the aqueous radioprotectant formulation comprises ascorbate in a concentration of at least 1 mM to 100 mM.

14. The composition of claim 10, wherein the saccharide is selected from the group consisting of glucose, mannose, fructose, melizitose, N-acetyl-D-glucosamine, sucrose or trehalose.

15. The composition of claim 14, wherein the aqueous radioprotectant formulation comprises mannose in a concentration of at least 1 mM to 100 mM.

16. The composition of claim 14, wherein the aqueous radioprotectant formulation comprises sucrose in a concentration of at least 10 mM to 1000 mM.

17. The composition of claim 10, wherein the aqueous radioprotectant formulation comprises a buffering agent; and has a pH of 6 or below.

18. The composition of claim 17, wherein the buffering agent is selected from the group consisting of citrate, tris (hydroxymethyl)aminomethane (TRIS) and tartrate.

19. The composition of claim 10, wherein the aqueous radioprotectant formulation comprises a surfactant.

* * * * *